United States Patent [19]

Nishikori et al.

[11] Patent Number: 5,259,365

[45] Date of Patent: Nov. 9, 1993

[54] ENDOSCOPE EXAMINATION APPARATUS

[75] Inventors: Toshiaki Nishikori, Sagamihara, Japan; Yukio Nakajima; Masahiro Kawashima, both of Hamburg, Fed. Rep. of Germany; Stuart M. Greengrass; Christopher Parker, both of Southend-on-Sea, United Kingdom; Shuichi Takayama; Kenichiro Sanagai, both of Hachioji, Japan; Shinichi Nishigaki, Tokyo, Japan; Nobuaki Akui, Hino, Japan; Tatsuya Yamaguchi, Hino, Japan; Takeaki Nakamura, Hino, Japan; Masaaki Hayashi, Hachioji, Japan; Akira Takano, Oume, Japan

[73] Assignee: Olympus Optical Co., Ltd., Tokyo, Japan

[21] Appl. No.: 942,339

[22] Filed: Sep. 9, 1992

Related U.S. Application Data

[63] Continuation of Ser. No. 557,049, Jul. 25, 1990, abandoned.

[30] Foreign Application Priority Data

| Jul. 26, 1989 | [JP] | Japan | 1-194756 |
| Aug. 1, 1989 | [JP] | Japan | 1-201012 |
| Sep. 26, 1989 | [JP] | Japan | 1-251417 |
| Sep. 26, 1989 | [JP] | Japan | 1-251419 |

[51] Int. Cl.⁵ ................................................ A61B 1/00
[52] U.S. Cl. ..................................... 128/4; 5/600
[58] Field of Search ............... 128/4, 6, 376, 897; 269/322-328; 5/60, 82 R, 600

[56] References Cited

U.S. PATENT DOCUMENTS

| 4,529,185 | 7/1985 | Gutierres | 269/326 |
| 4,601,284 | 7/1986 | Arakawa et al. | 128/6 |
| 4,768,241 | 9/1988 | Beney | 5/60 |
| 4,854,301 | 8/1989 | Nakajima | 128/4 |
| 4,957,121 | 9/1990 | Icenogle et al. | 5/82 R |
| 4,998,972 | 3/1991 | Chin et al. | 128/6 |

FOREIGN PATENT DOCUMENTS

| 0413988 | 2/1991 | European Pat. Off. | 269/322 |
| 2042899 | 8/1979 | Fed. Rep. of Germany | 269/327 |
| 60-156461 | 8/1985 | Japan . | |
| 63-143301 | 9/1988 | Japan . | |
| 64-83239 | 3/1989 | Japan . | |
| 64-86930 | 3/1989 | Japan . | |

Primary Examiner—Ralph Lewis
Attorney, Agent, or Firm—Armstrong, Westerman, Hattori, McLeland & Naughton

[57] ABSTRACT

An endoscope examination apparatus includes a bed on which a subject lies, a device separately positioned from the bed and used for an endoscope examination, a control device provided in the bed for controlling the device and a connecting device extended from the bed and connected to the device for operatively connecting the device and the control device.

13 Claims, 21 Drawing Sheets

ENDOSCOPE EXAMINATION APPARATUS

This application is a continuation of application Ser. No. 07/557,049 filed Jul. 25, 1990, (now abandoned).

BACKGROUND OF THE INVENTION

1. Field of the Invention

The present invention relates to an endoscope examination apparatus having an endoscope examination bed.

2. Related Art Statement

Recently, there has come into extensive use of an endoscope whereby the internal organs in the body cavity are observed by inserting an elongated insertable part into the body cavity, or whereby various treatments can be taken by using a treatment tool inserted into a treatment tool channel according to demand.

When an endoscope is used, endoscope peripheral devices such as a light source device, an air and water supplying device and a high frequency cautery device are needed. These devices are usually stored in a cart or the like and are placed beside a bed so that an operator can operate these devices and/or so that an endoscope can be connected with these devices. However, if these peripheral devices are arranged on the same side of the bed as of the operator, these devices tend to become obstacles and hinder an endoscope examination.

In order to cope with this, a bed with attached devices needed for an endoscope examination has been proposed as shown in the Gazettes of Japanese Patent Laid Open Nos. 156461/1985, 83239/1989 and 86930/1989.

However, if various functions are included in a bed, it is inconvenient in that the bed becomes larger and electric devices are liable to get wet or dirty from the body fluid, dirt or the like of a patient.

Also, in the Gazette of Japanese Patent Laid Open No. 143301/1988, an apparatus is disclosed in that an operating panel of a video processor, which is a separate body from a bed, is removably provided to a bed. However, this apparatus has a problem in that a cable for connecting the operating panel and the video-processor is arranged apart from the bed without passing through the bed and therefore gets in the way.

Also, generally, since there is only one panel for operating the peripheral devices, it is troublesome for a team comprising the operator and nurses to operate the operating panel. Further, it is difficult to position the operating panel in accordance with the contents of the examination and the maneuverability of the panel is inconvenient.

Also, the peripheral devices are generally placed at a certain interval away from the operator and nurses so as not to hinder them. The operator and nurses connect an endoscope and treatment tools and so forth with the peripheral devices so that they can pursue an endoscope examination such as an insertion of an endoscope into the body cavity and ensuing observation, and/or carry out a treatment by using the treatment tools. Although such an endoscope examination is accompanied by an adjustment of a light source device and/or a high frequency burning device, the adjustment is done while operators are standing. Therefore, there is a problem in that the operator and nurses become quite exhausted if the endoscope examination lasts for several hours. There is also a problem in that the conducting of the examination is inconvenient because the peripheral devices are arranged at some distance from the operator and nurses.

Further, the endoscope and treatment tools can be taken out of a storage place and/or cart at the time of the endoscope examination. However, in the case in which an endoscope and treatment tools are taken out in this way, it is troublesome to carry them to a patient's bed and there is a possibility that the endoscope might hit another device or the like and be broken while it is being moved.

OBJECT AND SUMMARY OF THE INVENTION

A purpose of this invention is to provide an endoscope examination apparatus in which devices used for an endoscope examination are not included in an endoscope examination bed and can be easily controlled.

Another object of this invention is to provide an endoscope examination apparatus having readily operable devices used for an endoscope examination.

A further object of this invention is to provide an endoscope examination apparatus which can reduce the fatigue of a person who operates devices used for an endoscope examination.

Yet another object of this invention is to provide a workable endoscope examination apparatus in which it is not necessary to carry an endoscope and treatment tools.

An endoscope examination apparatus of this invention comprising a bed on which a subject lies and devices used for an endoscope examination is provided with the devices being positioned separately from the bed, a control device in the bed for controlling the devices and a connecting device for connecting the devices and the control means, and the connecting device includes a part extended from the bed and connected the devices.

Also, an endoscope examination apparatus of this invention may be provided with an operating device on the outer peripheral part of the bed for operating the devices and a connecting device, comprising a plurality of connectors on the peripheral part of the bed, for removably connecting the devices and the operating device.

Further, the endoscope examination apparatus of this invention may be provided with a first connecting device for operatively connecting the devices and the control device, the operating device and a signal transmitting device for transmitting signals and receiving them by using radio and light between the control device and the operating device.

Further, the endoscope examination apparatus of this invention may be provided with the operating device in a chair movably attached to the bed.

Further, the endoscope examination apparatus of this invention may be provided on the bed with an insertion body which is inserted into the body cavity of a subject for carrying out the endoscope examination.

The other features and advantages of this invention will be apparent from the following explanation.

BRIEF DESCRIPTION OF THE DRAWINGS

FIG. 1 is a perspective view showing a bed and peripheral devices.

FIG. 2 is a block diagram showing the construction of the peripheral devices.

FIG. 3 is a perspective view showing a bed and peripheral devices when a video-scope is used.

FIG. 4 is a perspective view showing a bed and peripheral devices when a fiberscope is used.

FIG. 5 is a block diagram showing a control system for a video-scope control device.

FIG. 6 is a perspective view of a sub-operating panel.

FIGS. 7 (A) to (D) are illustrations showing examples of suboperating panel displays.

FIG. 8 is an illustration showing the structure of a bed.

FIG. 9 is an illustration showing a connecting part of an operating panel.

FIG. 10 is a perspective view of a bed.

FIG. 11 is a perspective view showing a bed and an operating unit.

FIG. 12 is a block diagram showing a signal transmitting system from an operating unit to a control device.

FIG. 13 is a perspective view of an endoscope examination apparatus.

FIG. 14 is a view in the direction of the arrow A in FIG. 13.

FIG. 15 is an illustration showing the inner construction of an endoscope examination apparatus.

FIG. 16 is an illustration showing the construction of an endoscope examination apparatus.

FIG. 17 is a perspective view showing an outline of an endoscope examination apparatus.

FIG. 18 is a perspective view showing a bed of the first example.

FIGS. 19 to 21 relate to the second example.

FIG. 19 is a perspective view of a bed.

FIG. 20 is a view in the direction of the arrow B in FIG. 19.

FIG. 21 is an illustration showing a bed being used in FIG. 19.

FIG. 22 is a perspective view of a third example of a bed.

FIG. 23 is a perspective view of a bed of the first example.

FIGS. 24 and 25 relate to the second example.

FIG. 24 is a perspective view showing a part of a bed.

FIG. 25 is a perspective view showing a cassette.

FIG. 26 is a perspective view of a bed of the third example.

FIG. 27 is an illustration showing a bed of the first example.

FIG. 28 is an illustration showing a bed of the second example.

FIG. 29 is an illustration of a bed of the third example.

FIGS. 30 and 31 relate to the fourth example.

FIG. 30 is a perspective view of a bed.

FIG. 31 is a sectional view of a monitor stand.

FIG. 32 is a perspective view of a bed.

FIG. 33 is an illustration showing a driving part of a bed.

FIG. 34 is an illustration showing the tip part of an insertion part of an endoscope.

DETAILED DESCRIPTION OF THE PREFERRED EMBODIMENTS

Figure 1:
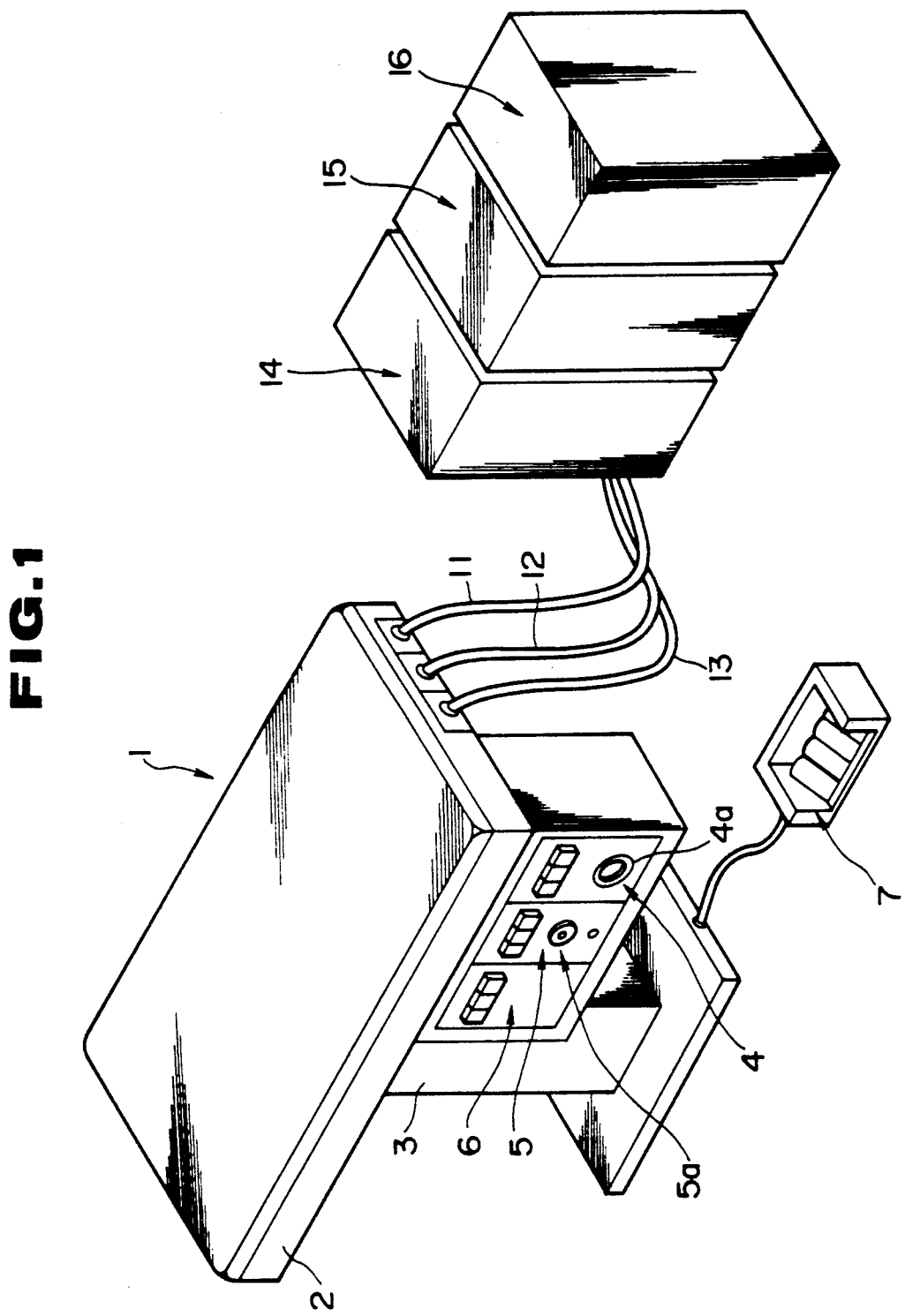
FIGS. 1 and 2 relate to the first embodiment of this invention.
Figure 2:
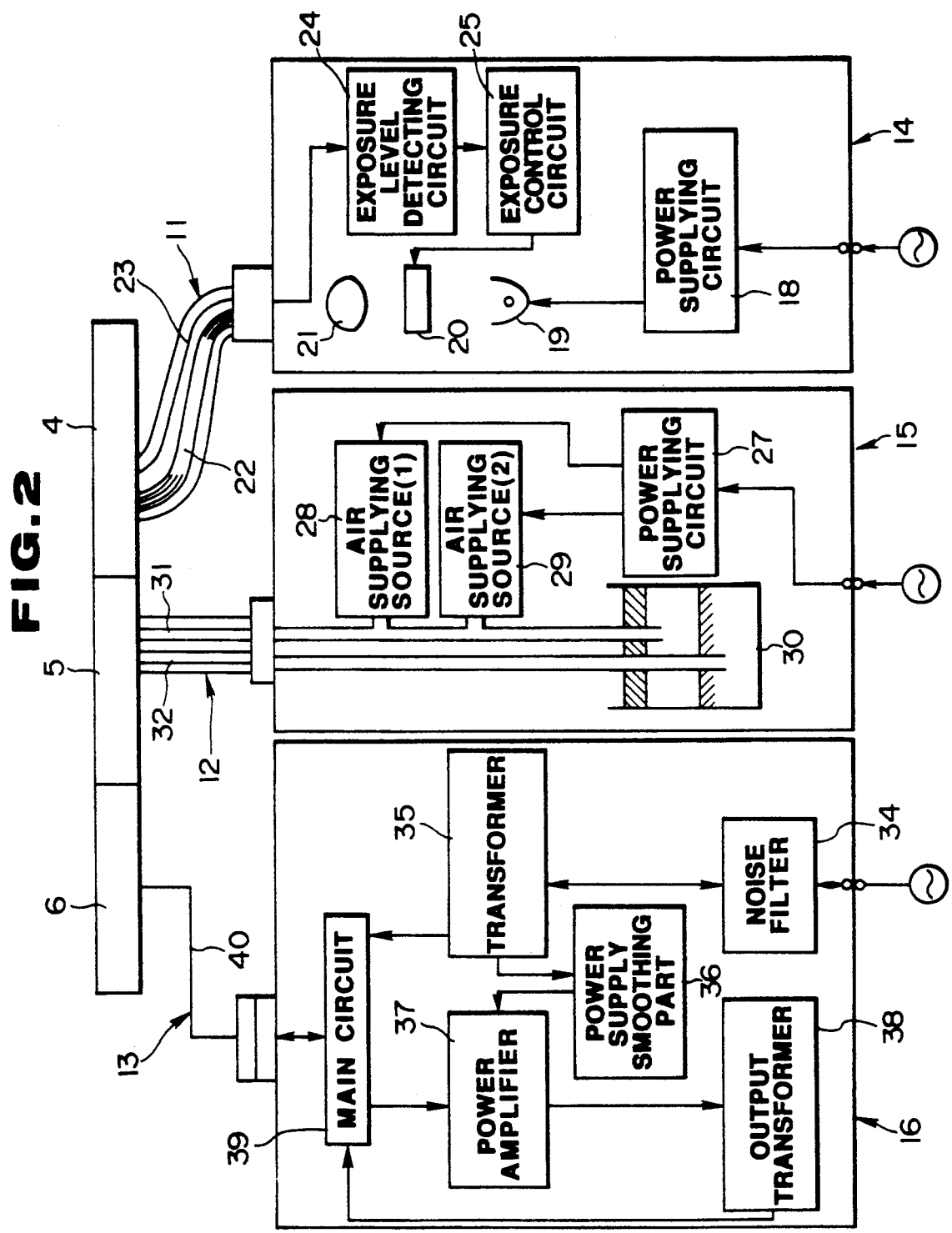

FIGS. 1 and 2 show the first embodiment of this invention.

As shown in FIG. 1, an endoscope examination apparatus is provided with an endoscope examination bed 1 which comprises a bed body 2 on which a subject lies, a supporting part 3 for supporting the bed body 2, a light source control part 4 comprising three control means and an operating means attached to the bottom of the bed body 2, an air and water supplying device control part 5 and a high frequency cautery device control part 6. An illuminating light emitting end part 4a is provided in the light source device control part 4. An air and water supplying channel connection part 5a is provided in the air and water supplying device control part 5. A light guide connector of an endoscope can be connected to the illuminating light emitting end part 4a. An air and water supplying channel of an endoscope is connected to the air and water supplying channel connection part 5a. Also, a foot switch 7 is connected to the bottom of the supporting part 3.

Provide to the side of the bed body 2 are a light source device 14, an air and water supplying device 15 and a high frequency cautery device 16. The three devices are used for an endoscope examination and are connected through cables 11, 12 and 13, respectively. The three cables comprise the first connecting means.

As shown in FIG. 2, the light source device control part 4, the air and water supplying device control part 5 and the high frequency cautery device control part 6 are connected to the light source device 14, the air and water supplying device 15 and the high frequency cautery device 16 through the cables 11, 12 and 13, respectively.

The light source device 14 comprises a power supplying circuit 18 connected with an outer power supply and a lamp 19 supplied with electric power from the power supplying circuit 18. The light emitted from the lamp 19 is converged by being passed through an iris 20 and through a condenser 21, and enters an incident end of a light guide 22 inserted in the cable 11. An emitting end of the light guide 22 is connected, to the illuminating light emitting end part 4a in the light source device control part 4. Also, in the cable 11, a cord 23 connecting the light source device control part 4 and a circuit in the light source device 14 is inserted. Then, through the cord 23, the light source device 14 can be turned on and off and the amount of light can be controlled by the light source device control part 4. Also, the signal from a light amount detecting means, which is not illustrated, provided in the endoscope is fed to an exposure level detecting circuit 24 provided in the light source device 14 through the cord 23. The output of the exposure level detecting circuit 24 is fed to an exposure control circuit 25 for driving the iris 20. Then, according to the exposure level detected by the exposure level detecting circuit 24, the amount of light is automatically adjusted by the iris 20 controlled by the exposure control circuit 25.

The air and water supplying device 15 is provided with a power supplying circuit 27 connected with an outer power supply, an air supplying source (1)28 and an air supplying source (2)29 connected with the power supplying circuit 27 and a tank 30 for storing water. Also, in the cable 12, an air supplying channel 31 connected to the air and water supplying channel connection part 5a and a water supplying channel 32 are included. The air supplying channel 31 is connected to the air supplying source (1)28, the air supplying source (2)29 and the upper space of the tank 30. Also the water supplying channel 32 is connected to the tank 30. Then, by controlling the air supplying sources 28 and 29, air or water can be supplied through the air supplying channel 31 or the water supplying channel 32, respectively. The air supplying &sources 28 and 29 can be controlled by the air and water supplying device control part 5 through a cord, which is not illustrated, included in the cable 12.

The high frequency cautery device 16 is provided with a noise filter 34 connected with the outer power supply, a transformer 35 connected with the noise filter 34, a power supply smoothing part 36 connected with the transformer 35, a power amplifier 37 connected with the power supply smoothing part 36, an output transformer 38 connected with the power amplifier 37 and a main circuit 39 connected with the high frequency cautery device control part 6 through a cord 40 included in the cable 13. The main circuit 39 may be connected with an electrode which is not illustrated. The electrode is supplied with a cautery current from the outer power supply through the noise filter 34, the transformer 35, the power supply smoothing part 36, the power amplifier 37, the output transformer 38 and the main circuit 39. The main circuit 39 switches the output waveform of the cautery current and controls the power amplifier 37 so as to control the output. The main circuit 39 is controlled by the high frequency cautery device control part 6. Further, the main circuit 39 is supplied with electric power from the transformer 35.

Also, the foot switch 7 is connected with the main circuit 39 in the high frequency cautery device 16 and the cautery current can be also controlled by the foot switch 7.

Thus, in this embodiment, the light source device 14, the air and water supplying device 15 and the high frequency cautery device 16 comprising the endoscope peripheral devices used for an endoscope examination are positioned apart from the bed 1, and the control parts 4, 5 and 6 of the devices 14, 15 and 16, respectively, the parts 4, 5 and 6, and devices 14, 15 and 16 are provided in the bed 1. Therefore, according to the present embodiment, the bed 1 does not become larger and electric devices are not dirtied by the body fluid, dirt or the like of a patient, and also the endoscope peripheral devices can be easily controlled.

Further, in addition to the control parts 4, 5 and 6 provided in the bed 1, the illuminating light emitting end part 4a at which an endoscope is connected to the light source device 14 and the air and water supplying device 15, and the air and water supplying channel connection part 5a are provided in the bed 1 so that it is not necessary for the devices 14, 15 and 16 to be placed on the same side of the bed as of the operator. Therefore, these devices do not become obstacles to the operation.

Also, since the cables 11 to 13 comprising the first connecting means extend from another side of the bed body 2 and are connected to the devices 14 to 16, these cables 11 to 13 do not become obstacles.

Also, in this embodiment, the endoscope peripheral devices are not limited only to the devices shown in the embodiment, but may also be an electronic endoscope light source device, a video processor (signal processing device) and a suction device.

Further, in this embodiment, a single unit comprising the control parts of each device and a connecting part to the endoscope is provided in the bed; however, the bed may be simplified by providing only the above mentioned connecting part in the bed.

As explained above, according to this embodiment, it is advantageous that endoscope peripheral devices are not included in the bed and also that the devices can be easily controlled because a control means for controlling endoscope peripheral devices which are separated from an endoscope examination bed is provided.

FIGS. 3 to 7 show the second embodiment of this invention.

Figure 3:
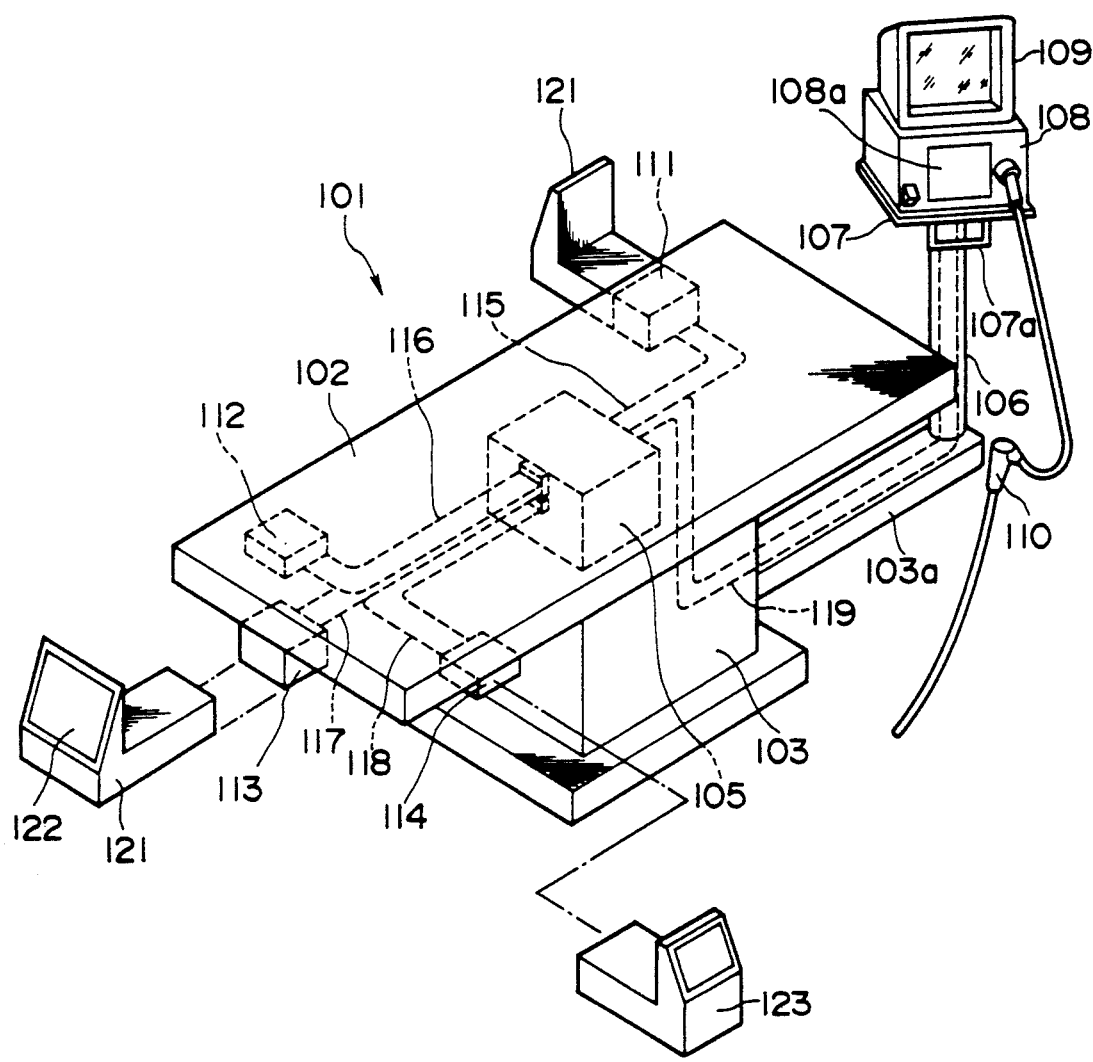
FIGS. 3 to 7 relate to the second embodiment of this invention.

As shown in FIG. 3, an endoscope examination apparatus is provided with an endoscope examination bed 101 which comprises a bed body 102 on which a subject lies and a supporting part 103 for supporting the bed body 102. Four connectors 111, 112, 113, and 114 are fitted to the sides of the bed body 102. Also, a control device 105 comprising a control means and having a CPU is contained in the endoscope examination bed 101. This control device 105 and connectors 111 to 114, respectively, are connected through cables 115 to 118 comprising the second connecting means. Also, the positions in which the connectors 111 to 114 are optional and may be moved to alternative positions by using a rail outlet.

A stand prop 106 is fitted on an extended part 103a of the supporting part 103. A stand 107 is provided on the stand prop 106. A grip 107a is fitted to the stand 107. Then, a video-scope control device 108, containing a light source and a signal processing circuit which comprising devices used for an endoscope examination, is put on the stand 107 and a monitor 109, connected to the video-scope control device 108, is put on the video-scope control device 108. An operating panel 108a is provided on the video scope control device 108. Also, a video-scope 110 is connected to the video-scope control device 108, which is connected to the control device 105 in the bed 101 through a cable 119 comprising the first connecting means. Also, all of the cables 115 to 119 are arranged in the bed 101.

A data input device 123 such as a sub-operating panel 121 comprising an operating means, and a keyboard can be connected to any of the connectors 111 to 114. In FIG. 3, it is shown that sub-operating panels 121 and 121 are connected to the connectors 111 and 113, respectively, and the data input device 123 is connected to the connector 114.

Figure 5:
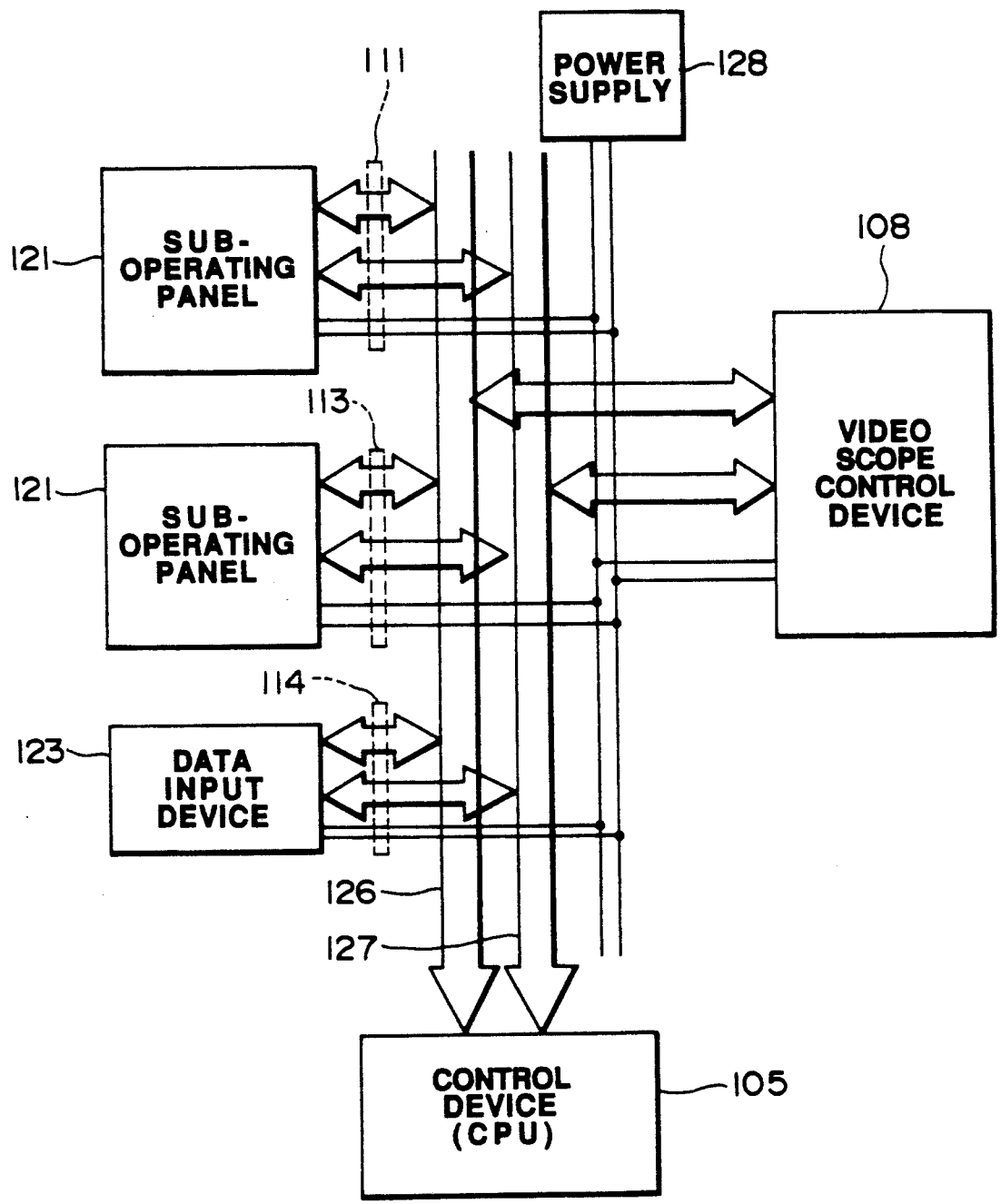

As shown in FIG. 5, a data bus 126 and address bus 127 of the CPU of the control device 105, and a power supply 128 are connected to the connectors 111 to 114 (connector 112 is not illustrated), respectively, and the video-scope control device 108. Even if each sub-operating panels 121 and the data input device 123 is connected to any of the connectors 111 to 114, the video-scope control device 108 can be operated and controlled through the control device 105 by the sub-operating panels 121 and the data input device 123.

Figure 6:
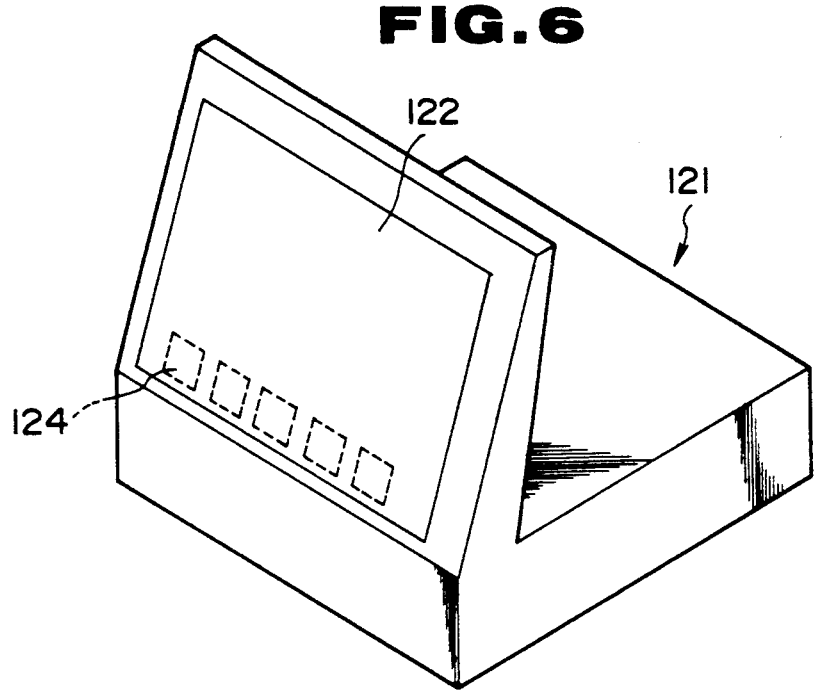
Figure 7A:
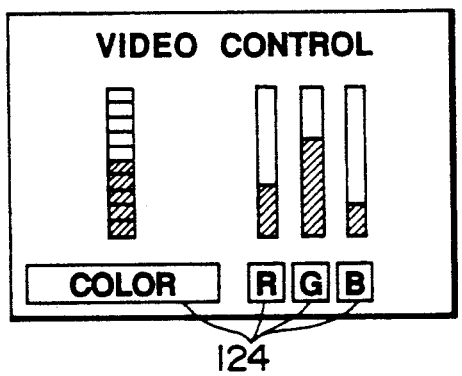
Figure 7B:
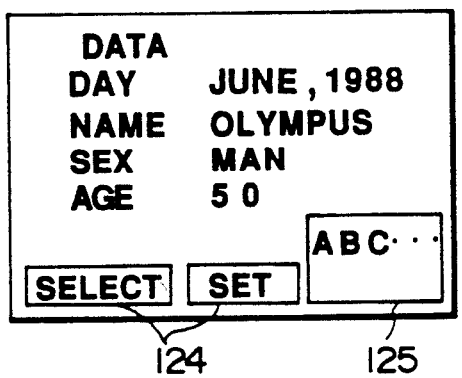
Figure 7C:
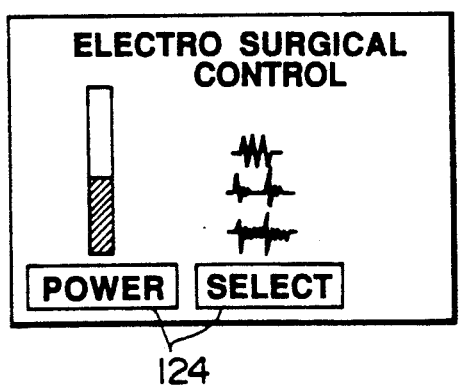
Figure 7D:
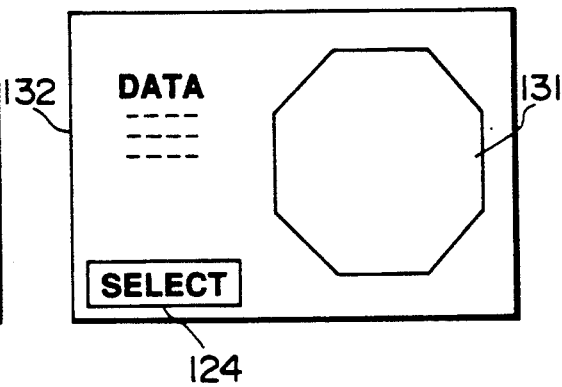

As shown in FIG. 6, the sub-operating panel 121 has a liquid crystal display 122 and a transmitting light type touch switch 124 is provided on the liquid crystal display 122. Also, the display 122 serves both as a display and a monitor for displaying an endoscope image obtained by the video-scope 110. FIG. 7 is an example of the display of the liquid crystal display 122. FIGS. 7(A) to (C) represent control modes. FIG. 7(A) is an example of the case of video control. Each color level is displayed and each color tone can be controlled by the touch switch 124. FIG. 7(B) is an example of the case of data input and a full keyboard 125 is displayed. A date, name, sex, age and so on can be input by the keyboard and can be also displayed. FIG. 7(C) is an example of the case of connecting with an electric scalpel. By the touch switch 124, an output control and output waveform can be chosen and an output and output waveform can be displayed. FIG. 7(D) is an example of the case of using the display 122 as a monitor. An endoscope image 131 and various data 132 are displayed and the each control mode can be chosen by the touch switch 124.

Figure 4:
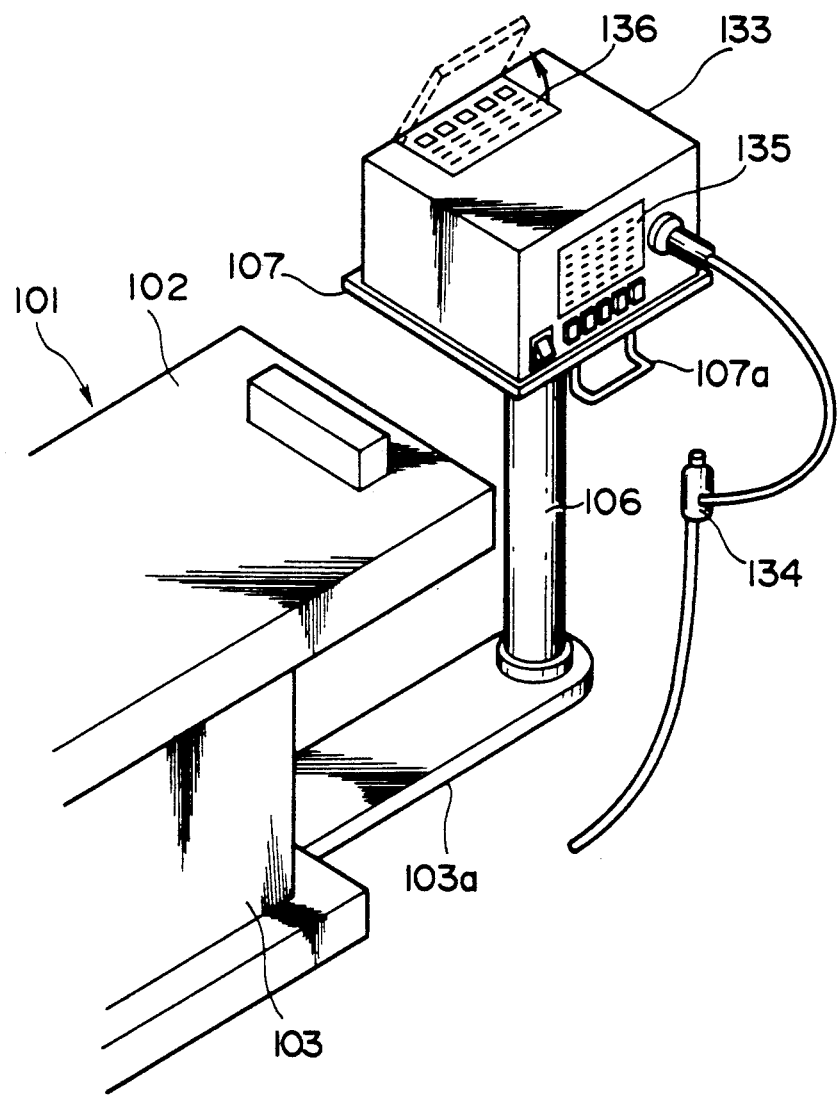

Also, the endoscope examination bed 101 of this embodiment can be used when a fiberscope is used. A state using a fiberscope is shown in FIG. 4. In this case, a light source device 133 is put on the stand 107. A fiberscope 134 is connected to the light source device 133. On the light source device 133, an operating panel 135 is provided on the front part and a sub-operating panel 136 is provided on the upper surface. The sub-operating panel 136 is operated by an assistant and can be covered when the panel is not used.

In this manner, according to this embodiment, because a plurality of connectors 111 to 114 being connectable to the sub-operating panel 121 and the data input device 123 are provided in the endoscope examination bed 101, it becomes possible to control the video-scope control device 108 on a plurality of parts by fitting a plurality of sub-operating panels 121 to the endoscope examination bed 101. Therefore, for example, when an operator and nurses work as a team, the operating panel can be watched and operated so that the maneuverability is improved.

Also, according to the contents of an examination, the sub-operating panel 121 and the data input device 123 can be arranged in proper positions so that the maneuverability is improved.

Further, since the liquid crystal display 122 serves as both an operating panel and an endoscope image display monitor, the operating panel can be operated in a proper position and an endoscope image can be seen.

Since the control device 105 and the cables 115 to 119 are contained in the endoscope examination bed 101, they do not get in the way.

Figure 8:
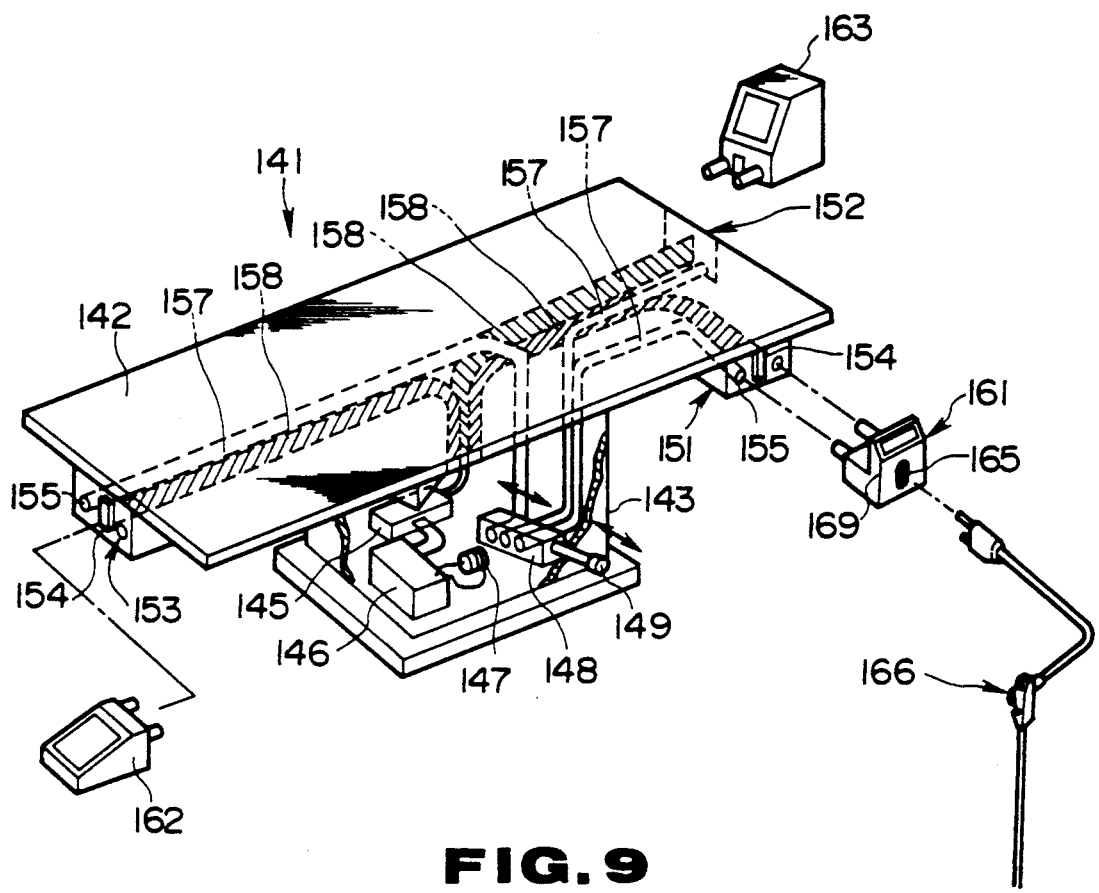
FIGS. 8 to 10 relate to the third embodiment of this invention.
Figure 9:
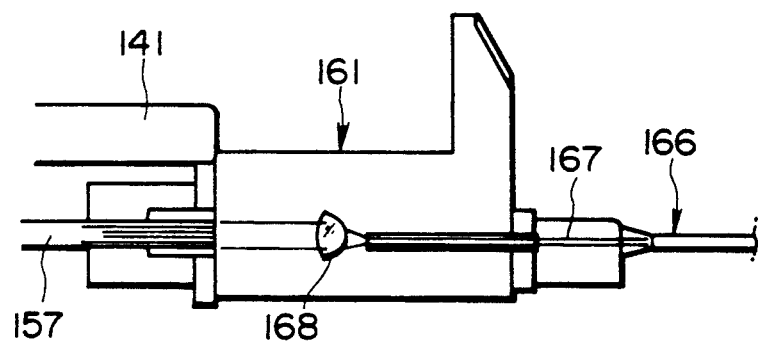
Figure 10:
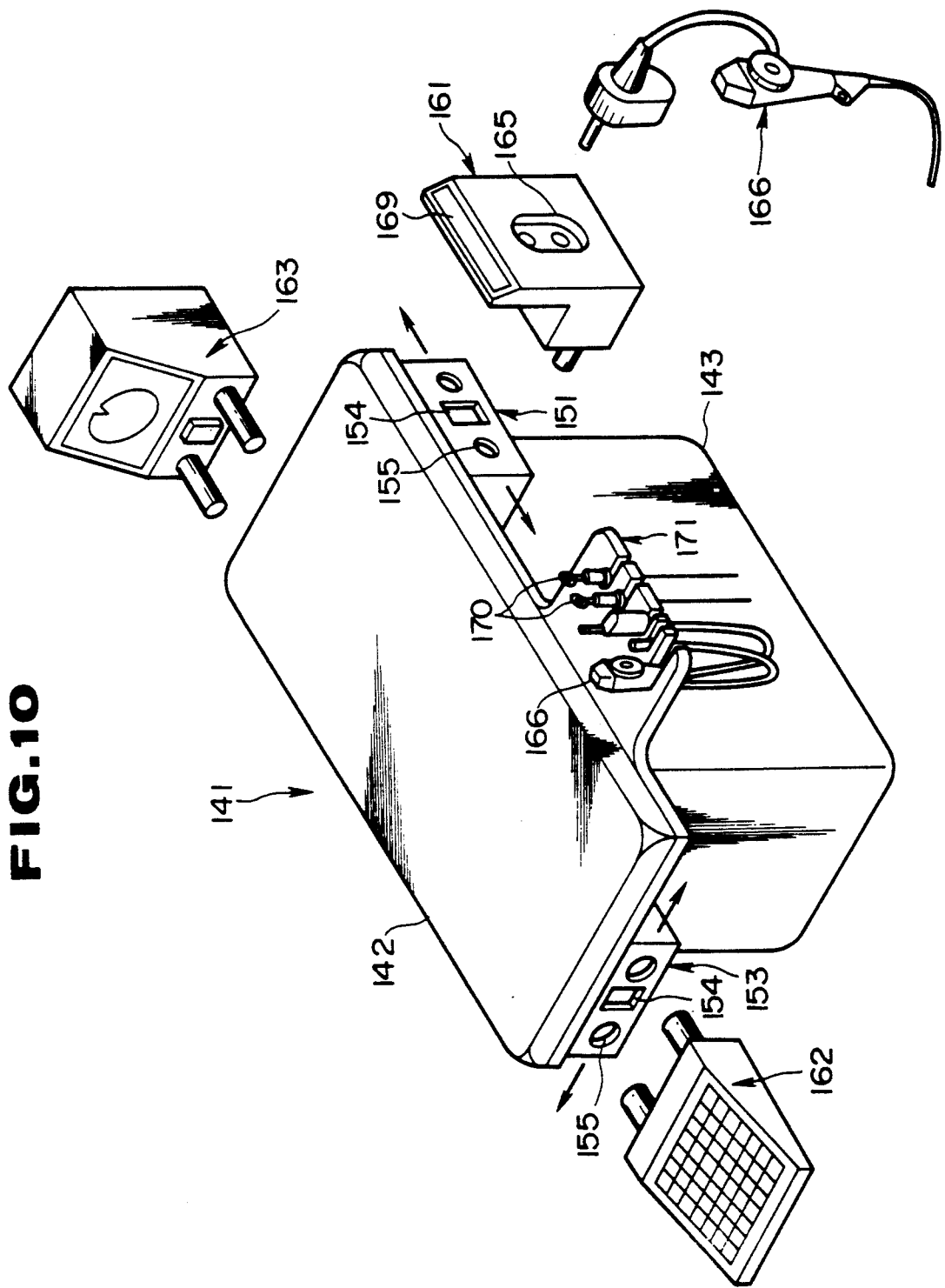

FIGS. 8 to 10 relate to the third embodiment of this invention.

As shown in FIGS. 8 and 10, an endoscope examination bed 141 of this embodiment comprises a bed body 142 on which a subject lies and a supporting part 143 for supporting said bed body 142. Three connectors 151, 152 and 153 are fitted to the sides of said bed body 142. These connectors 151, 152 and 153 comprise an electric connector part 154 and a light guide connector part 155, respectively. Also, the positions to which the connectors 151, 152 and 153 are fitted are optional and can be slidable so that the connectors can be moved to alternative positions.

In said supporting part 143, a control unit 145 having a CPU comprising a device used for the endoscope examination and the control means of the device, a power supply, a control unit 145 having a video signal processing device, a lamp power supply starter 146 connected to the control unit 145 and a lamp 147 connected to the lamp power supply starter 146 are provided. Parallel luminous flux is emitted from said lamp 147. Further, a cooler which is not illustrated is fitted on the lamp 147. A light guide selecting unit 148 is placed opposite to the lamp 147. On the light guide selecting unit 148, each incident end part of three bed side light guides 157 is placed in the horizontal direction and fitted. Each light guide 157 is contained in the bed 101 and each emitting end is connected to each light guide connector part 155 of connectors 151, 152 and 153. A light guide selecting lever 149 is fitted to the light guide selecting unit 148. The light guide selecting unit 148 is moved to the direction of the arrangement of the incident end of the light guide by pushing and pulling the lever 149, and the incident end of one of the three light guides 157 faces the lamp 147. In FIG. 8, it is shown that the incident end of the light guide 157 connected to the connector 151 faces the lamp 147.

Also, the electric connector part 154 of said connectors 151, 152 and 153 is connected to said control unit 145 through a cable 158.

An operating panel 161, a keyboard 162 and a monitor 163 can be connected to any of said connectors 151, 152 and 153. The operating panel 161 has a scope connector receiver 165 so that an endoscope (video-scope) 166 is connectable to the scope connector receiver 165. As shown in FIG. 9, the illuminating light transmitted by the bed side light guide 157 is converged by a condenser 168 provided in the operating panel 161 and enters the incident end of the light guide 167 of said endoscope 166. Also, an operating part 169 comprising a touch switch is provided on said operating panel 161 and the operating part 169 is electrically connected to the electric connector part 154.

The keyboard 162 and the monitor 163 are electrically connected to the electric connector part 154, respectively.

As shown in FIG. 10, in this embodiment, a hanger 171 on which the endoscope 166, treatment tools 170, and/or a suction device can be hung is provided on the side of the bed body 142.

Further, other than the operating panel 161, the keyboard 162 and the monitor 163, treatment tools such as a data input device and a electric scalpel, and an unit comprising only the operating parts of a light source, a video signal processing device, an electric scalpel and so on, are connectable to said connectors 151 to 153.

In this embodiment, the operating panel 161, the keyboard 162 and the monitor 163 are connected to the optional connectors 151, 152 and 153 when an endoscope examination is carried out. The endoscope 166 is connected to said operating panel 161. Also, by the light guide selecting lever 149, the light guide selecting unit 148 is made to move so that illuminating light can enter the light guide 157 connected to the connector to which the operating panel 161 is connected. The illuminating light emitted from the lamp 147 enters a light guide 167 of the endoscope 166 through the light guide 157 and a condenser 168 in the operating panel 161. The output signal of the endoscope 166 is supplied to the control unit 145 through the operating panel 161 and the cable 158 so that the signal is processed to be a video signal. The video signal output from the control unit 145 is supplied to the monitor 163 through the cable 158 so that a subject image is displayed on the monitor 163.

Each output signal of the operating part 169 of the keyboard 162 and the operating panel 161 is supplied to the control unit 145 through the cable 158, respectively. Then, a light source, a video signal processing device, a monitor, an electric scalpel output and others can be controlled by the CPU in the control unit 145.

In this manner, according to this embodiment, since the operating panel 161, the keyboard 162, the monitor 163 and others are provided in a plurality of the connectable connectors 151 to 153 in the endoscope examination bed 141, the operating panel 161, the keyboard 162, the monitor 163 and others can be placed on the optional positions in the endoscope examination bed 141 according to the contents of the examination so that the maneuverability is improved.

As described above, according to the second and third embodiments, it becomes possible that operations in a plurality of parts is carried out by fitting a plurality of operating parts to a plurality of fitting parts provided in or to the endoscope examination bed and operating positions are 00, also selected, so that it is advantageous that the maneuverability of endoscope peripheral devices can be improved.

Figure 11:
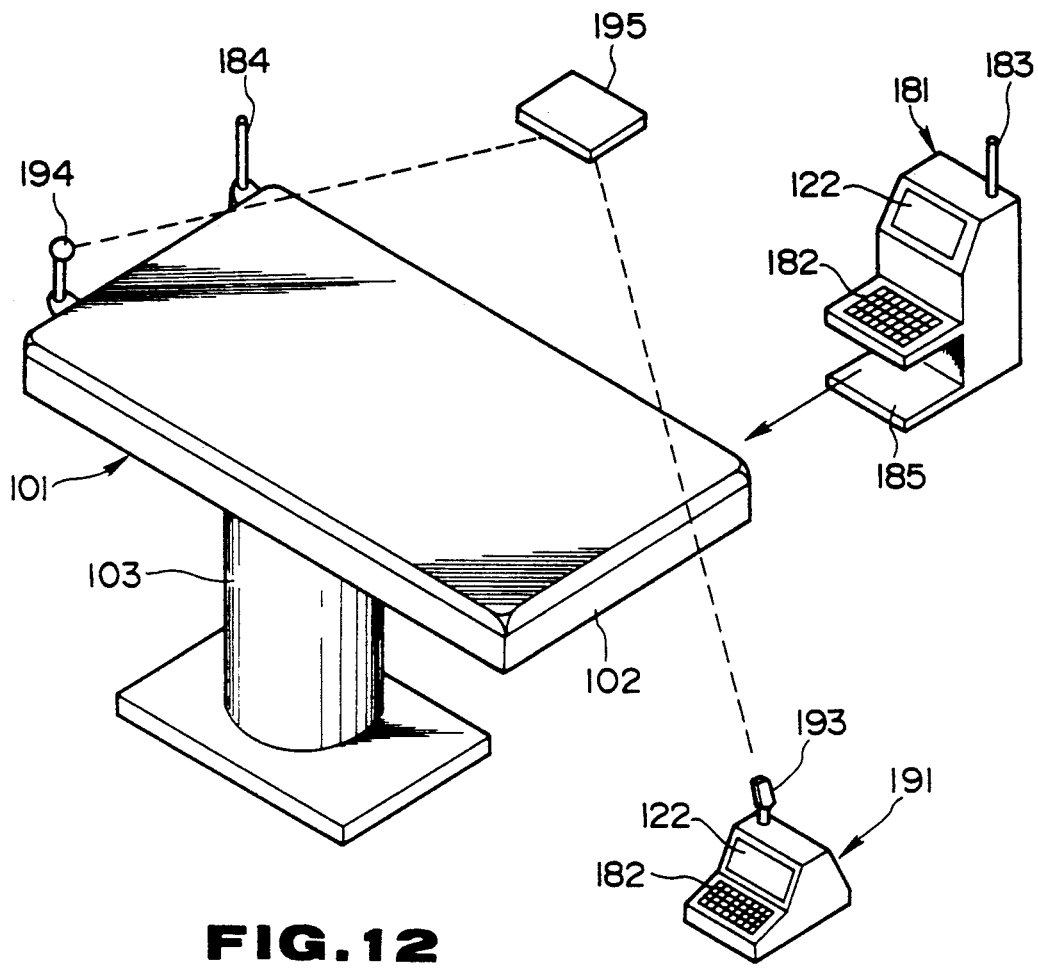
FIGS. 11 and 12 relate to the fourth embodiment of this invention.
Figure 12:
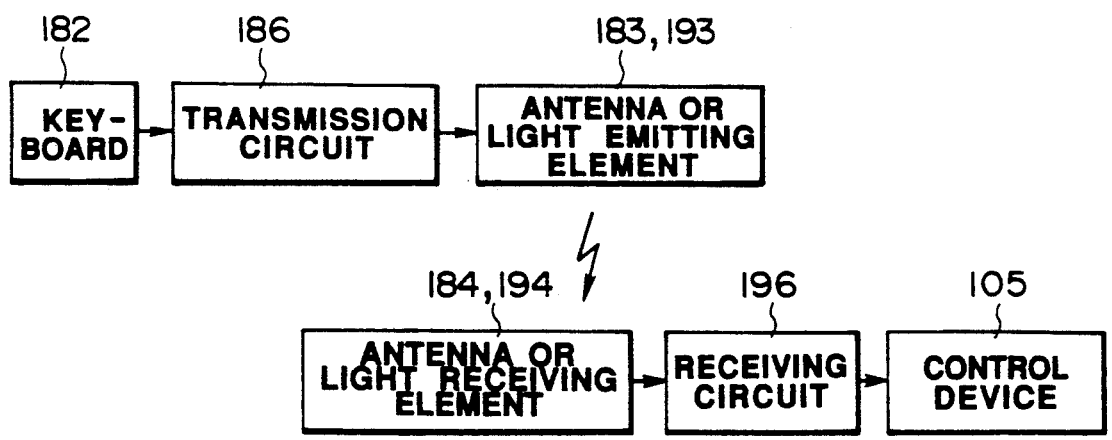

FIGS. 11 and 12 show the fourth embodiment of this invention.

In this embodiment, as shown in FIG. 11, operating units 181 and 191 are provided as an operating means. One operating unit 181 is provided with a keyboard 182, the display 122, an antenna 183 and a clamp 185. This operating unit 181 can be removably fixed to the side of the bed body 102 by said clamp 185. Also, in the example shown in FIG. 11, the keyboard 182 and the display 122 face the inside of the bed 101 in the condition that the operating unit 181 is fixed to the bed body 102. However, the keyboard 182 and the display 122 may be made to face the outside of the bed 101 in the condition that the position of the clamp 185 is reversed and the operating unit 181 is fixed to the bed body 102.

Also, the other operating unit 191 is provided with the keyboard 182, the display 122 and a light emitting element 193.

As shown in FIG. 12, the keyboard 182 of each of the operating units 181 and 191 is connected to said antenna 183 or light emitting element 193 through a transmission circuit 186 provided in each of the operating units 181 and 191. Then, the information input by said keyboard 183 is modulated at the transmission circuit 186. In the case of the operating unit 181, the information is sent out from the antenna 183 as a radio wave, and in the case of the operating unit 191, it is sent from the light emitting element 193 as a light signal.

Also, an antenna 184 receiving the radio wave from said antenna 183 and a light receiving element 194 receiving the light signal from said light emitting element 193 are provided on the side of the bed body 102. Also, on the ceiling, a mirror 195 is provided to reflect the light signal from said light emitting element 193 and to guide to said light receiving element 194.

In the same way as in the the second embodiment, the control device 105 is provided in the bed 101. As shown in FIG. 12, said antenna 184 and a light receiving element 194, respectively, are connected to said control device 105 through a receiving circuit 196. Then, the information received by said antenna 184 and light receiving element 194 is demodulated by the receiving circuit 196 and sent to the control circuit 105.

Other structure is shown in the the same manner as the second embodiment.

According to this embodiment, signals are transmitted and received by using radio or light between the operating units 181 and 191 for operating the video-scope control device 108, therefore, the video-scope control device 108 is controllable at an optional position and the maneuverability is improved.

Other operations and effects are in the same manner as shown in the second embodiment.

Figure 13:
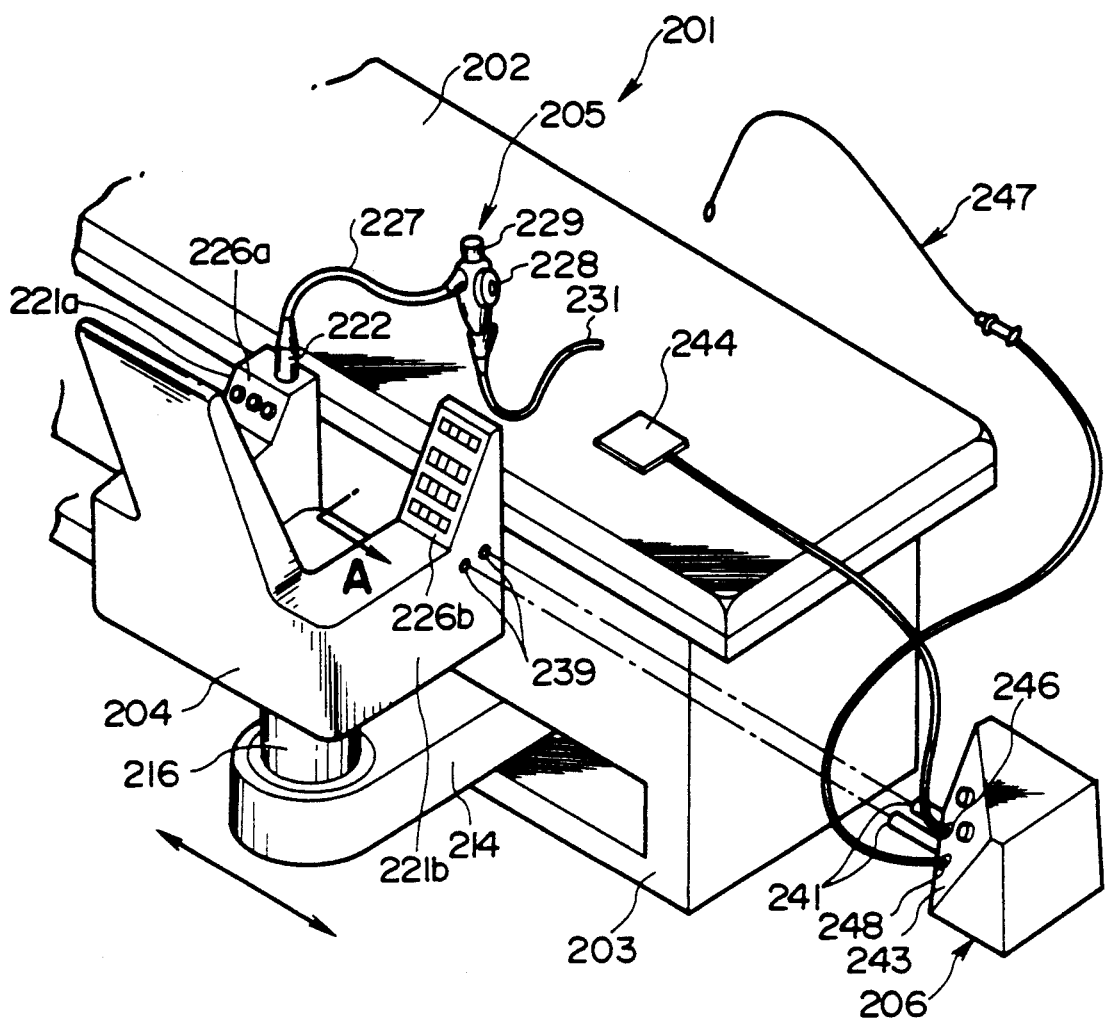
FIGS. 13 to 15 relate to the fifth embodiment of this invention.
Figure 14:
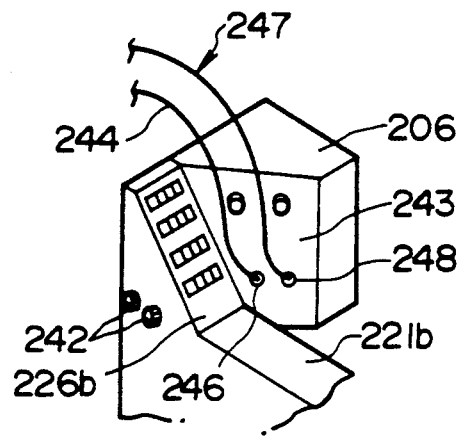
Figure 15:
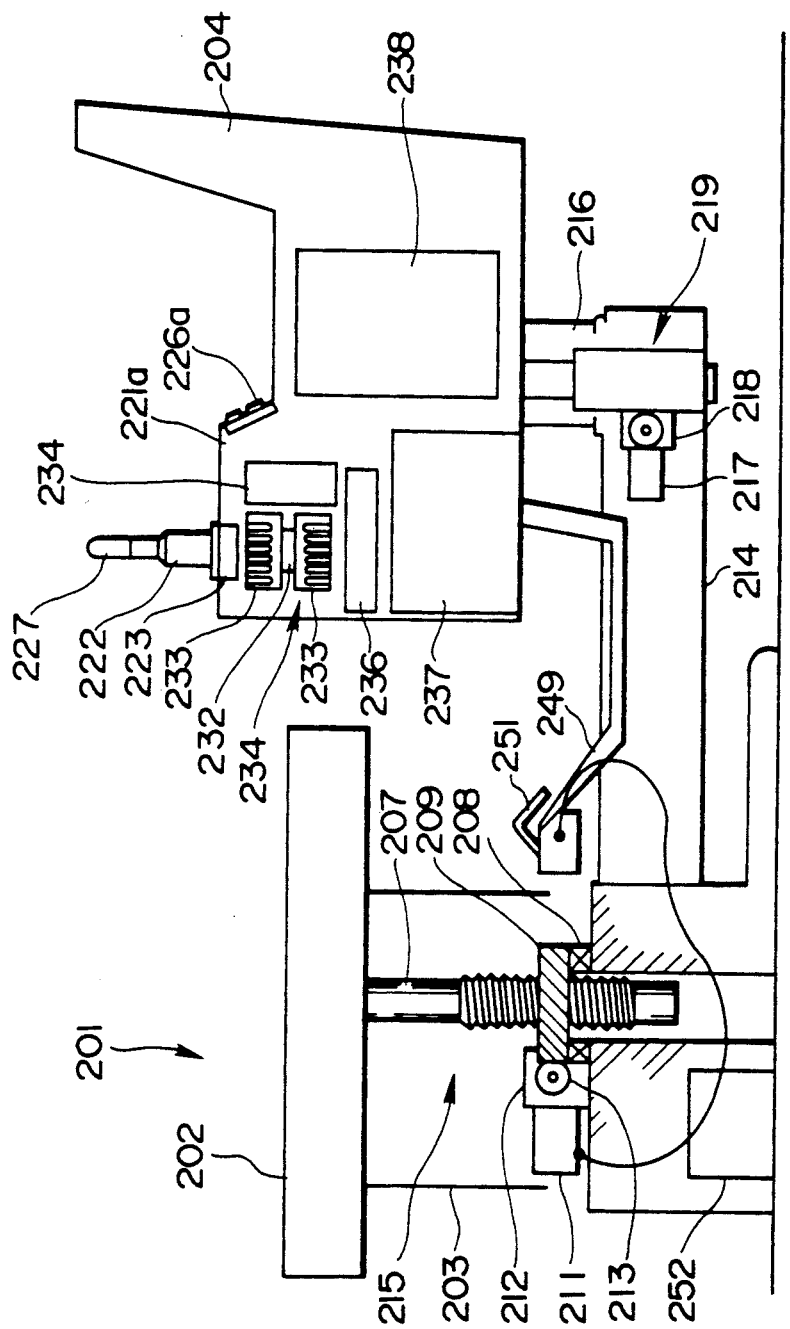

FIGS. 13 to 15 show the fifth embodiment of this invention.

An endoscope examination apparatus 201 in this embodiment is provided with a patient's bed 202, a supporting part 203 for supporting the bed 202, a doctor's chair 204 which is movably supported by the supporting part 203, a high frequency cautery device 206 comprising a device used for an endoscope examination which is removably connected to the doctor's chair 204 and an endoscope 205 connected to the doctor's chair 204.

In the center of the under surface of said bed 202, a screw pole 207 is projected downward and engaged with a toothed wheel (not illustrated) provided in the rotary center of a worm wheel 209. This worm wheel 209 is removably supplied by a bearing 208 provided in the supporting part 203 which is fixed on the floor surface.

Also, in the supporting part 203, a motor 211 for lifting and lowering the bed is fitted and the motor 211 is connected with a toothed wheel box 212. A worm gear 213 for engaging with said worm wheel 209 is provided to an output axis of the toothed wheel box 212. The screw pole 207, the bearing 208, the worm wheel 209, the motor 211, the worm wheel box 212 and the worm gear 213 form a bed lifting device 215. When the motor 211 is driven, the worm gear 213 and the worm wheel 209 rotate and the screw pole 207 engaging with the worm wheel 209 moves up and down so that the bed lifting device 215 can lift and lower the bed 202.

A chair arm 214 is projected out the side of said supporting part 203 and said doctor's chair 204 is fitted to the tip part of the arm 214. In a prop 216, a chair lifting device 219 formed of a motor 217, a toothed wheel box 218 and a toothed wheel (not illustrated) can lift and lower the chair 204.

Arm 214 can be moved in the lengthwise direction of the bed 202 by a chair moving device (not illustrated) provided in the supporting part 203.

The doctor's chair 204 has elbow rests 221a and 221b on both sides. On the surface of one elbow rest 221a, a connector receiver 223 connecting with a light guide connector 222 of an endoscope 205 and a light source operating panel 226a of a light source device 224 which is contained in the elbow rest 221a are provided. When a doctor sits on the chair, this light source operating panel 226a is supplied within the doctor's reach without difficulty.

Also, the light guide connector 222 is provided at the rear end of a light guide cable 227, which is extended from an operating part 228. At the end of the operating part 228, an eyepiece part 229 is provided, and at the other end, an insertion part 231 is provided, respectively.

A lamp 232 as a light source part, heat sinks 233 and 233 and a fan 234 for cooling the heat sinks 233 and 233 are provided in said elbow rest 221a. Further, a starter 236, a switching regulator 237, a printed circuit board 238 and so forth are contained in the elbow rest 221a.

Also, on the surface of the other elbow rest 221b, a light source operating panel 236b is supplied within the doctor's reach without difficulty when the doctor sits on the chair. On the outer side of the elbow rest 221b, through holes 239 and 239 passing through and reaching the doctor's side are perforated. Fitting rods 241 and 241 projected from the box of the high frequency cautery device 206 are inserted into the through holes 239 and 239. As shown in FIG. 14, nuts 242 and 242 are spirally fitted to the tip parts of the fitting rods 241 and 241 which expose to the doctor's side so that the high frequency cautery device 206 is removably fixed to the elbow rest 221b. Where the high frequency cautery device 206 is fitted to the elbow rest 221b, an operating panel 243 faces the doctor's side and the operating panel is supplied within the doctor's reach without difficulty when the doctor sits on the chair. On this operating panel 243, not only an operating knob but also a connector 246 for connecting with an electrode board 244 on the patient's side and a connector 248 for connecting with a treatment tool 247 are provided. Also, a connector(not illustrated) for electric supply is provided to the fitting rod 241. Thus, when the high frequency cautery device 206 is fitted to the elbow rest 221b, an electric power can be supplied from the side of the bed.

A foot rest 249 on which the doctor rests his feet is provided. Further, a pedal switch 251 is provided at the tip part of the foot rest 249. This pedal switch 251 is connected to the bed lifting device 215, the chair lifting device 219 and a chair moving device (not illustrated) so that the bed 202 and the chair 204 are lifted, lowered and moved if the doctor steps on the pedal switch.

An insulating transformer 252 is provided in the supporting part 203 so that an electric power can be supplied to the light source device 224 and the high frequency cautery device 206.

The functions of the endoscope examination apparatus 201 formed as mentioned above will be explained as follows.

The doctor connects the light guide connector 222 of the endoscope 205 to the connector receiver 223 and moves the chair 204 in the lengthwise direction of the bed 202 in accordance with the examination object of the patient by stepping on the pedal switch 251 while the doctor sits on the chair 204. Further, a position to be examined is adjusted by lifting and lowering the bed 202 and the chair 204 by stepping on the pedal switch 251.

Then, the doctor inserts the insertion part 231 of the endoscope 205 into the body cavity and observes the object from the eyepiece part 229. In the case in which the quantity of light or the like of the light device 224 is adjusted, the adjustment is performed with the light source operating panels 226a and 226b provided in the elbow rests 221a and 221b.

Also, when a high frequency cautery is applied, the high frequency cautery device 206 is fitted to the elbow rest 221b and the electrode board 244 for the patient is connected to the connector 246 provided on the operating panel 243 of the high frequency cautery device 206 and then, the treatment tool 247 is connected to the connector 248. Next, a medical treatment is applied by inserting the treatment tool 247 into the body cavity through an endoscope. The output of the high frequency cautery device 206 can be adjusted with the knob provided on the operating panel 243.

In this embodiment, the doctor can perform the endoscope examination while the doctor sits on the chair 204 because devices needed for the endoscope examination are arranged around the doctor's chair 204 and even if the examination lasts for a long time, the fatigue of doctor can be reduced.

Also, since the operating panel and other devices are arranged within the doctor's reach, the maneuverability for performing the endoscope examination can be improved.

Further, in the above mentioned embodiment, the doctor's chair 204 can move in the lengthwise direction of the bed 202; however, the movement of the chair is not restricted by this movement and may be made to move around the bed 202. Also, not only the high frequency cautery device 206 is fitted to the elbow rest 221b, but also other devices used for the endoscope examination may be fitted to the elbow rest 221b.

As mentioned above, according to this embodiment, the fatigue of the doctor at the endoscope examination can be reduced and the maneuverability can be improved by providing at least one of devices needed for the endoscope examination and the operating means of the device to the doctor's chair.

Figure 16:
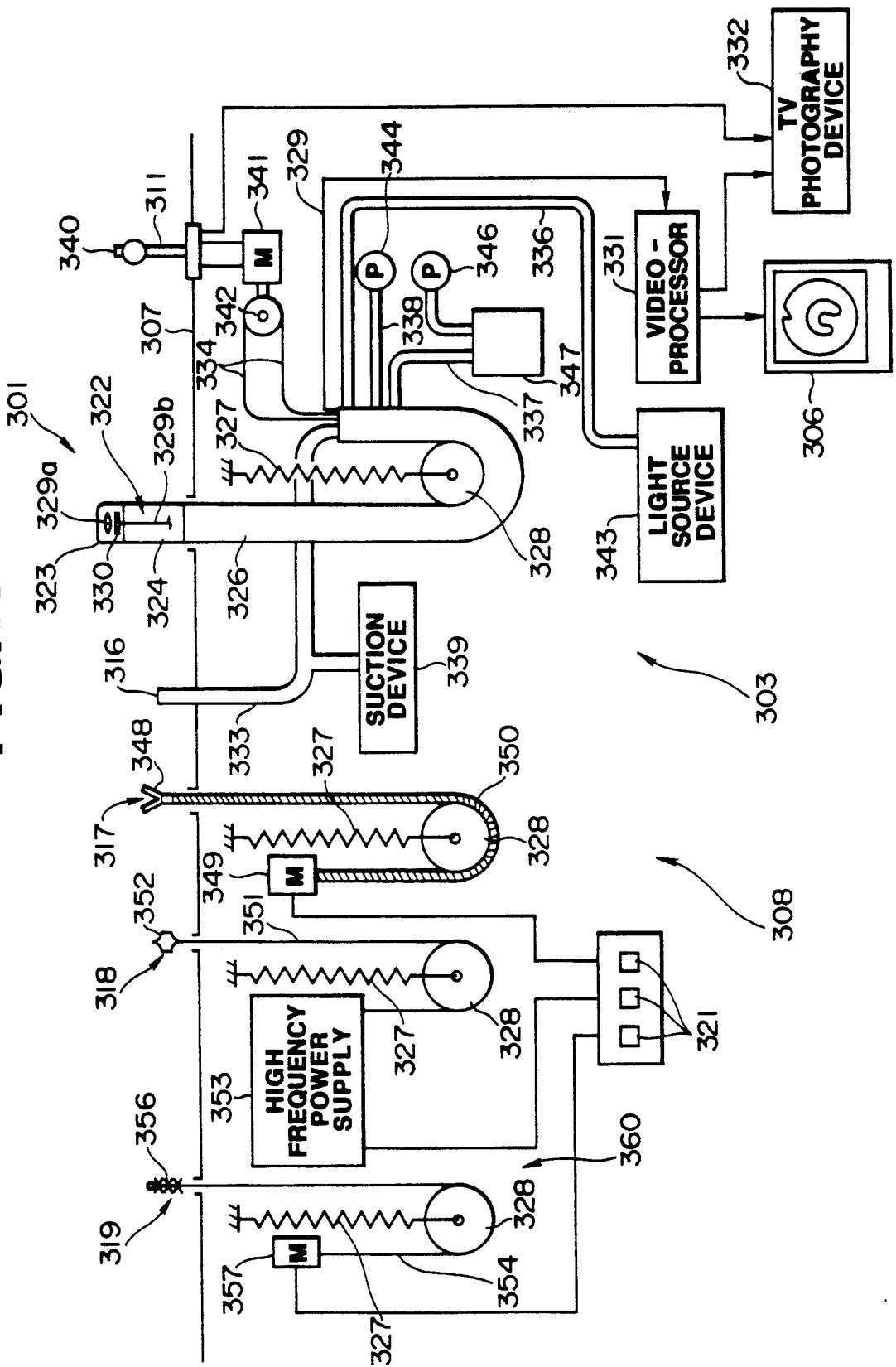
FIGS. 16 to 17 relate to the sixth embodiment of this invention.
Figure 17:
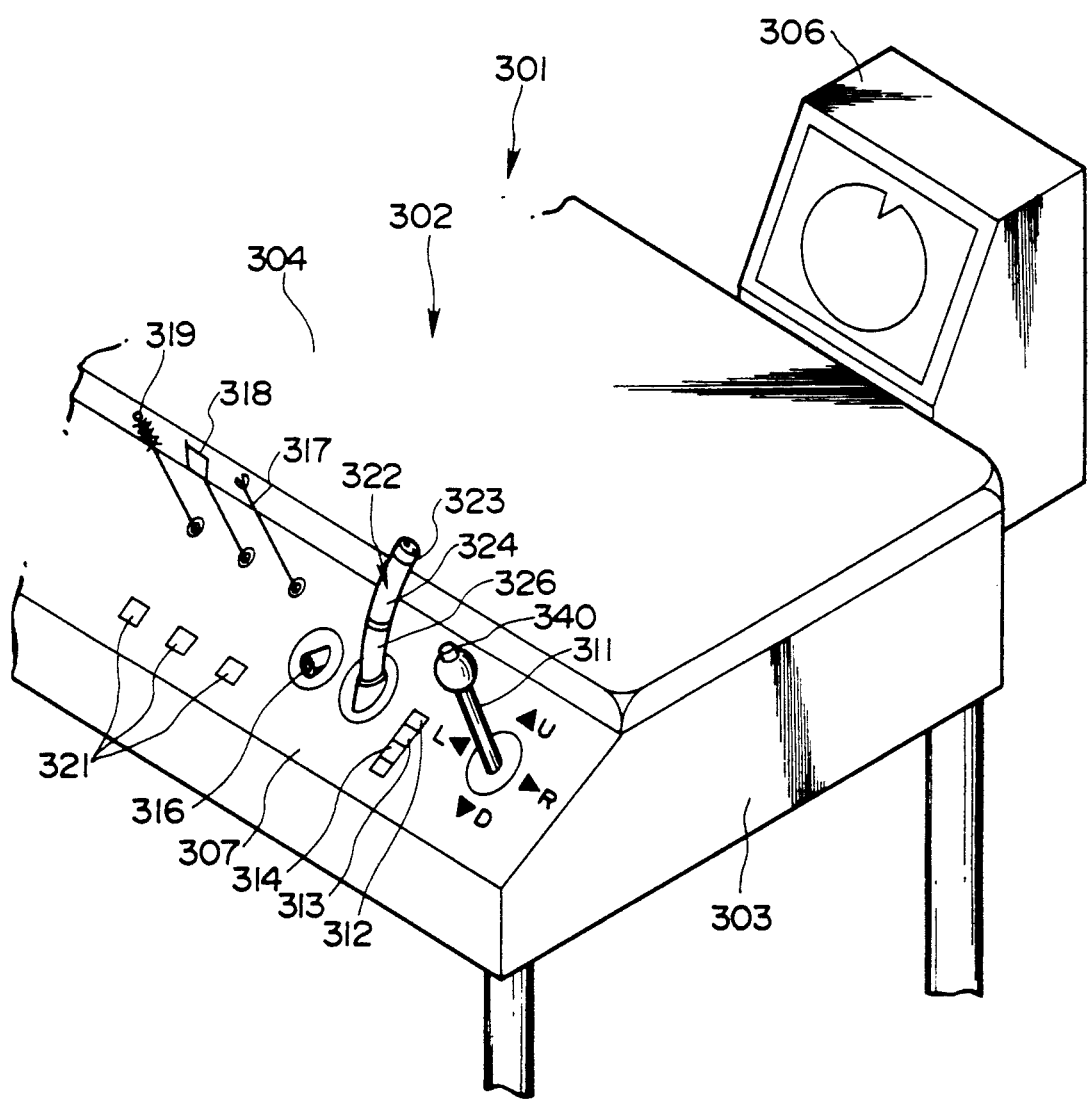

FIGS. 16 and 17 show the sixth embodiment of this invention.

In FIG. 17, an endoscope examination apparatus 301 includes a patient's bed 302 which comprises a bed body 303 and a bed surface part 304. A monitor 306 is fitted to one side of the bed body 303 so that the doctor who operates the endoscope at the bedside can observe an endoscope image.

An operating panel 307 is fitted to the other side of said bed body 303. On this operating panel 307, an insertion part 322 forming an endoscope body 308, a joy stick for bending operation 311, an air supplying button 312, an water supplying button 313, a suction button 314, an inlet for inserting treatment tools 316, biopsy forceps 317 as treatment tools, a high frequency snare 318, a cytology brush 319 and operation switches 321 are provided.

In FIG. 16, said insertion part 322 is formed into long and narrow shape, and an end part of the insertion part 322 is provided with a tip part 323 and the other end part is fixed to the bed body 303. A bending part 324 is linked to the tip part 323 and a flexible tube part 326 is linked to the bending part 324. The tip part 323 and the bending part 324 projected out the operating panel 307 and the flexible tube 326 in the bed body 303 is U-shaped by a roller 328 which is applied force upwards by a spring member 327 such as a coil spring.

Also, on said tip part 323, an objective lens 329a and a solid state imaging device 329b arranged on the focal position of this objective lens 329a are provided.

A signal line 329, connected to the solid state imaging device 330 which photoelectrically transfers an object image and outputs the image as an electric signal, is extended from the fixed other end part of said insertion part 322. This signal line 329 is connected to a video processor 331 contained in the bed body 303. The video processor 331 is connected to the monitor 306 and a TV photography device 332 so as to output a video signal to each device.

Further, a treatment tool insertion tube 333, bending operation wires 334 and 334, a light guide 336, a water supplying tube 337 and an air supplying tube 338 are extended from the other end part of said fixed insertion part 322.

A part of the treatment tool insertion tube 333 extended from the other end part of the insertion part 322 branches out into two. One of the branched tubes is led to said inlet 316 for inserting treatment tools 316 and the other tube is connected to a suction device 339. The treatment tool insertion tube 333 inserted into the insertion part 322 is led to an opening for treatment tools(not illustrated) provided at the tip part 323 so that the treatment tools are led into the body cavity. The suction device 339 is controlled with the suction button 314 so as to suck the blood or the like in the body cavity.

Said bending operation wires 334 and 334 is hung around a belt pulley 342 rotated by a bending operation motor 341. The motor 341 is input a control signal from said joy stick for bending operation 311 and the motor 341 rotates by inputting the control signal and the bending part 324 is bent by pushing and pulling the wires 334 and 334. Also, the joy stick 311 is provided with a release switch 340 and a release signal is input into said TV photography device 332 by operating the release switch 340 so that an endoscope image is recorded.

Said light guide 336 is connected to the light source device 343 contained in the bed body 303 and supplied with the illuminating light generated at the light source device 343. Also, the light guide 336 inserted into the insertion part 322 reaches the tip part 323 and the object is illuminated with illuminating light from a light guide emitting end surface (not illustrated).

The air supplying tube 338, which is connected to an air supplying pump 344 and inserted into the insertion part 322, opens its opening at the tip part 323. The air supplying pump 344 is controlled with said air supplying button 312.

The water supplying tube 337 is connected to a water supplying tank 346 which is applied pressure by the water supplying pump 346. The water supplying tube 337 inserted into the inserting part 322 is united with said air supplying tube 338 at the tip part 323. The water supplying pump 346 is controlled with the water supplying button 313.

Said biopsy forceps 317 comprise a sheath 350. An end of the sheath 350 is provided with a biopsy cup 348 projected out the operating panel 307 and the other end is connected with a motor for biopsy forceps 349. The sheath 350 in the bed body 309 is U-shaped by the roller 328 which is applied force upwards with the spring member 327 such as a coil spring.

Said high frequency snare 318 comprises a wire part 351. An end part of the wire part 351 is provided with a snare part 352 projected out the operating panel 307 and the other end part is connected with a high frequency power supply device 353. The wire part 351 in the bed body 303 is U-shaped by the roller 328 which is applied force upwards with the spring member 327.

Said cytology brush 319 comprises a wire part 354. An end part of the wire part 354 is provided with a brush part 356 projected out the operating panel 307 and the other end part is connected with a motor for cytology brush 357. The wire part 354 in the bed body 303 is U-shaped by the roller 328 which is applied force upwards with the spring member 327.

The operations of said motor for biopsy forceps 349, the high frequency power supply device 353 and the motor for cytology brush 357 are controlled with said operation switches 321 provided on the operating panel 307.

In the bed body 303, a storage part 360 for storing said insertion part 322 and treatment tools 317 to 319 are provided. The insertion part 322 and treatment tools 317 to 319 are applied force upwards with the spring member 327 and stored in the storage part 360 when the part and tools are not used.

The functions of the endoscope examination apparatus 301 formed as mentioned above will be explained as follows.

In the case in which an endoscope observation is performed, the insertion part 322 projected out the operating panel 307 is pulled. The roller 328 is applied force upwards by pulling the insertion part 322 and moved in the upwards direction in FIG. 16 so that the insertion part 322 is pulled out of the bed body 303. From the tip part 323, the insertion part 322 which is pulled out is inserted into the body cavity of a patient.

On the other hand, the illuminating light emitted from the light source device 343 enters the body cavity and illuminates the object through the light guide 336. The illuminated object forms an image in the solid state imaging device 329b with the objective lens 329a and this optical image is electrically converted and input into the video processor 331 as an electric signal through the signal line 329. In the video processor 331, the electric signal which is input is applied a predetermined signal processing so that the signal is input into the monitor 306 and the TV photography device 332 as a video signal. Then, an endoscope image is displayed on the monitor 306. The operator observes the endoscope image at the bedside while conducting the insertion.

In the case in which the bending part 324 is bent, the joy stick for bending operation 311 is operated and the motor for bending operation 341 is driven. The motor 341 rotates the belt pulley 342 and the bending part 324 is bent in the directions of up and down, and right and left by pushing and pulling the bending operation wires 334 and 334 which are hung around the belt pulley 342.

Also, in the case in which an endoscope image is needed recording, the release switch 340 provided at the joy stick 311 is operated. Then, a release signal is sent to the TV photography device 332 and the endoscope image is photographed.

Air is supplied by operating the air supplying button 312 provided on the operating panel 307. If the air supplying button 312 is operated, the air supplying pump 344 is driven and air is supplied to the body cavity through an air supplying tube 338. In the case of supplying water, a water supplying pump 346 is driven and a water supplying tank 347 is applied pressure, and therefore, the liquid in the water supplying tank 347 is supplied to the body cavity through the water supplying tube 337 by operating the water supplying button 313 provided on the operating panel 307 in the same manner. Suction is carried out in the same manner with the suction button 314 provided on an operating panel 307. The suction device 339 is driven by operating the suction button 314 so that the blood and other things are sucked through the treatment tool insertion tube 333.

In the case in which the treatment tools are used, the tools are inserted into an inlet for inserting treatment tools 316, for example, the biopsy forceps 317 are pulled out, inserted into the inlet from the side of the biopsy cup 348. By pulling out the biopsy forceps 317, the roller 328 applying force to the biopsy forceps 317 into an U-shape resists the spring of the spring member 327 and is moved in the upper direction in FIG. 16. When the biopsy cup 348 is projected out the tip part 323 through the tool insertion tube 333 and the operation switch 321 provided on the operating panel 307 is operated, a motor for operating the biopsy forceps 349 is driven and the biopsy cup 348 closes so that cells are picked. When the picking is completed, the biopsy forceps 317 are stored in a storage part 360 in the bed body 303 by the spring member 327.

Also, in the case in which the high frequency snare 318 used, the tools are inserted into the inlet for inserting treatment tools 316 in the same manner. By pulling out the high frequency snare 318, the roller 328 resists the spring of the spring member 327 and is moved upwards. When a snare part 352 is projected out the tip part 323 through the tool insertion tube 333 and the operation switch 321 is operated, a high frequency current is sent from the high frequency power supplying device 353 to the snare part 352 so that cautery stanching or the like is performed. When the treatment is completed, the high frequency snare 318 is stored in the storage part 360 in the bed body 303 by the spring member 327.

Further, in the case in which the cytology brush 319 is used, the cytology brush 319 is inserted into the inlet for inserting treatment tools 316 in the same manner as mentioned above. By pulling out the cytology brush 319, the roller 328 applied force upwards by the spring member 327 resists the spring and is moved upwards. When the cytology brush 319 is projected out the tip part 323 through the tool insertion tube 333 and the operation switch 321 is operated, a cytology brush motor 357 is driven and cells in the body cavity are picked by a brush part 356. When the picking is completed, the brush is stored in the storage place 360 in the bed body 303 by the spring member 327.

As mentioned above, when the treatment is completed, the insertion part 322 is stored in the storage place 360 in the bed body 303 by the spring member 327.

In this embodiment, since the insertion part 322 and treatment tools (biopsy forceps 317, high frequency snare 318 and cytology brush 319) are stored in the bed body 303, it is not necessary to move them from the place which is apart from the bed so that the risk of causing damage to these tools which is arises while the tools are moving can be eliminated.

Further, since the insertion part 322 and treatment tools are stored in the bed body 303 by the spring member 327 when the use of these tools is finished, it is not necessary to put them back so that time can be saved.

Further, since the light source device 343, the video processor 331, the monitor 306, the suction device 339, the air supplying pump 344, the water supplying pump 346, the water supplying tank 347 or the like are provided in the bed body 303, a space for arranging these devices is not needed so that a space of an examination room can be effectively used.

Also, the treatment tools in the above mentioned embodiment include the biopsy forceps 317, the high frequency snare 318 and the cytology brush 319; however, the treatment tools are not limited to the above mentioned and other tools may be used.

Further, the endoscope body 308 and treatment tools stored in the bed body 303 may be washed by providing a washing device in the bed body 303.

According to this embodiment, as mentioned above, it is not necessary to carry an endoscope and treatment tools to the patient's bedside by providing them in the bed so that the risk of causing damage to these tools by carrying them can be reduced and so that the maneuverability can be improved.

In addition to the peripheral devices, other devices such as treatment tools, mouthpiece and camera, accessories, medicines and others are used for the endoscope examination. Although these devices are generally stored in a cart and used beside the bed during an operation, said cart is, for example, positioned behind an operator so that it is troublesome for the operator to look behind to operate tools and to take accessories and so that it is also a problem for safety to keep the operator's eyes off the patient while he looks behind.

Then, FIGS. 18 to 22 show examples in which the operator can easily operate tools, accessories, medicines and so forth and can take them out without taking his eyes off the patient by providing a storage space in and under the endoscope examination bed for storing tools, accessories, medicines and so forth used for the endoscope examination.

Figure 18:
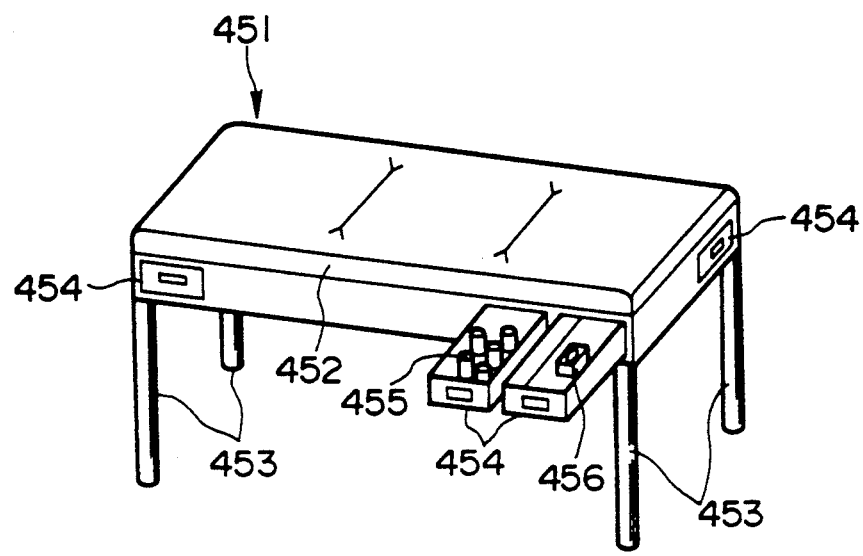
FIGS. 18 to 22 relate to an example in which a storage space for tools and so forth used for an examination is provided in or under a bed.

FIG. 18 shows a first example. A bed 451 of this example comprises a bed body 452 on which a subject lies and bed legs 453 for supporting the bed body 452. On the sides of the bed body 452, storage parts 454 consisting of a plurality of drawers are provided. Therefore, medicines 455, camera 456 and so on can be stored in the storage parts 454.

Figure 19:
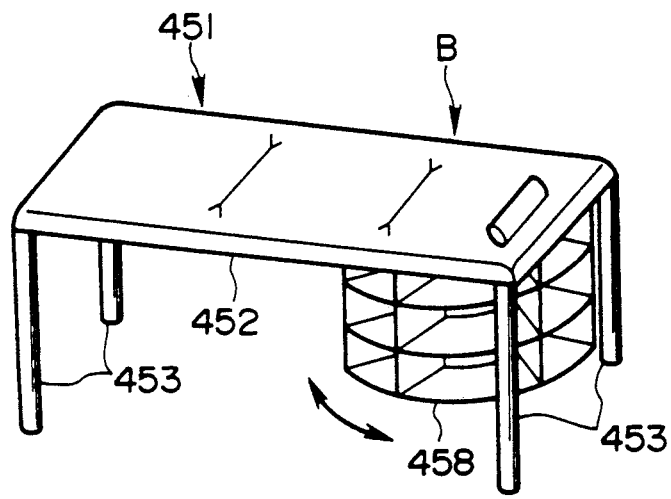
Figure 20:
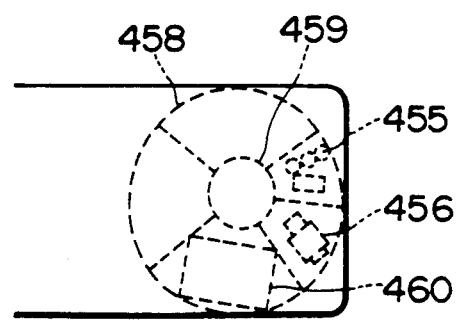
Figure 21:
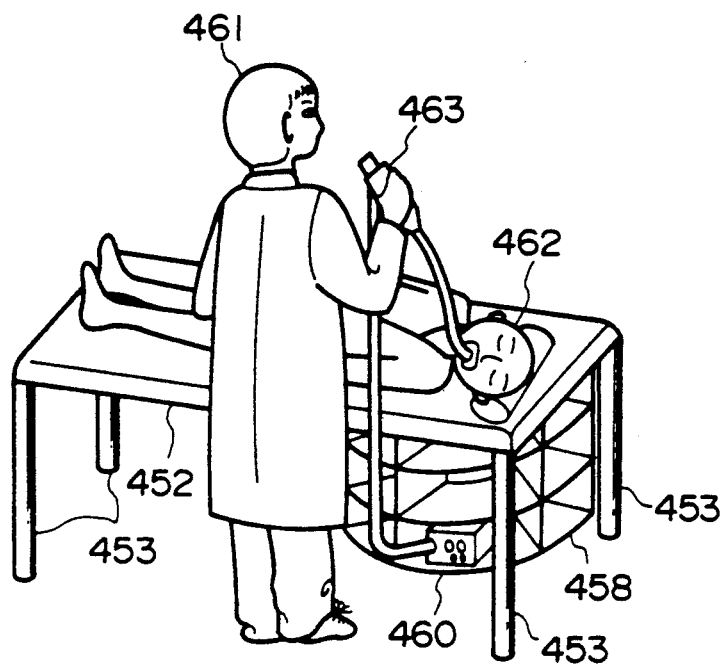

FIGS. 19 to 21 show a second example. In this example, a rotary rack 458 which can be rotated around an axis 459 are fitted under the bed body 452. The rotary rack 458 has a plurality of racks and each rack is partitioned into a plurality of storage parts as shown in FIG. 20. Therefore, the medicines 455, the camera 456, light source device 460 or the like can be stored in each storage part.

FIG. 21 shows a state that an endoscope examination is being performed while the light source device 460 is stored on said rotary rack 458. Also, in FIG. 21, a reference numeral 461 represents an operator, a reference numeral 462 represents a subject and a reference numeral 463 represents an endoscope.

In this manner, according to the second example, the part under the bed can be more effectively used.

Figure 22:
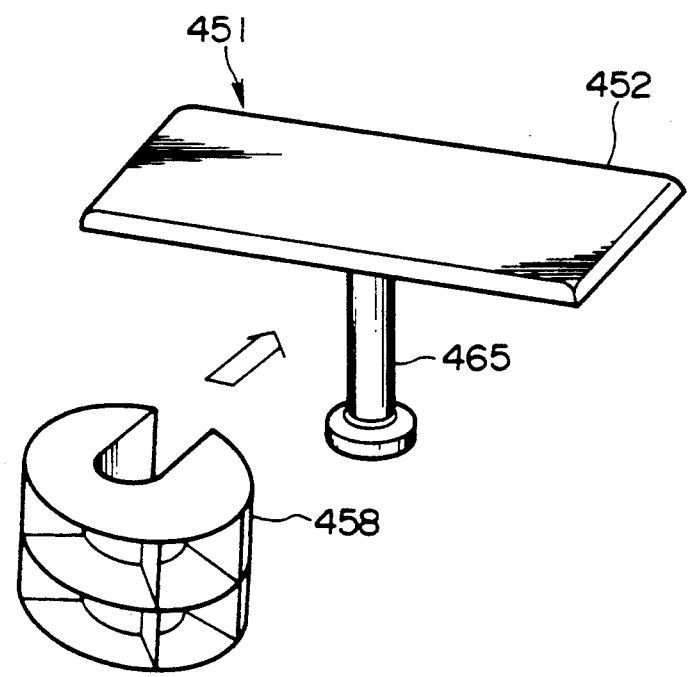

FIG. 22 shows a third example. In this example, a bed 451 comprises a bed body 452 and a column shaped supporting part 465 for supporting the bed body 452. The rotary rack 458 can be removably attached to said supporting part 465.

Thus, according to the third example, the rotary rack 458 on which the tools suitable for the examination were stored in advance of the examination can be exchanged according to the type of the examination and the subject, therefore, the time for preparing the examination can be shortened.

Up to the present, in the case in which treatment tools were used during an operation, it was necessary for nurses to hold the tools prepared before the operation and to wait because there was no place to put these tools near the bed. Also, in the same manner, there was no place to position an endoscope near the bed.

Then, FIGS. 23 to 26 show examples in which an operator can freely use tools and/or endoscope and temporarily put them without any help by providing a means for holding treatment tools and/or endoscope on the side of the bed.

Figure 23:
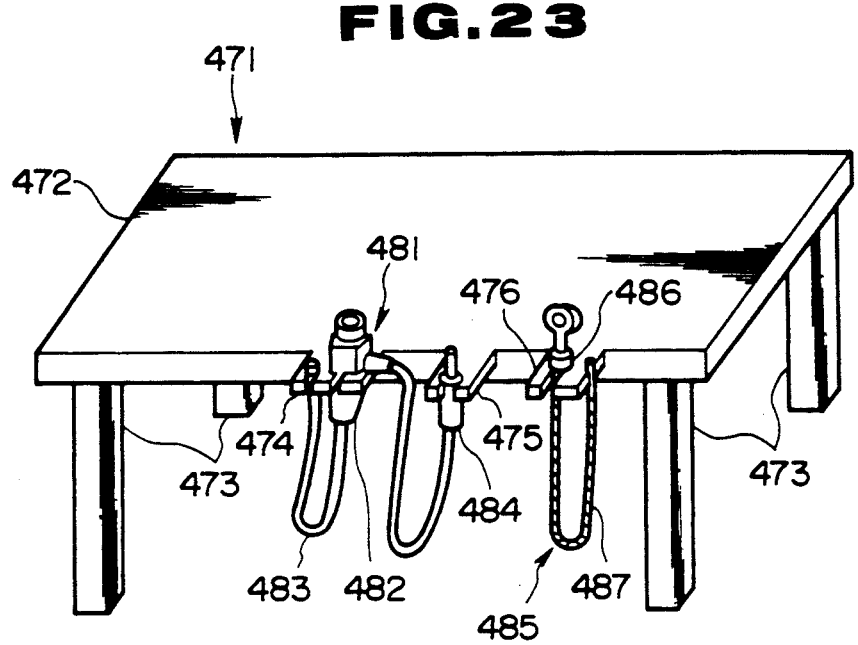
FIGS. 23 to 26 relate to an example in which a treatment tool or an endoscope is provided beside a bed.

FIG. 23 shows a first example. A bed 471 of this example comprises a bed body 472 an which a subject lies and bed legs 473 for supporting the bed body 472. On one side of the bed body 472, a scope hanger 474, a connector hanger 475 and a treatment tool hanger 476 are projected out the side and provided.

The scope hanger 474 has a slitting for holding an operating part 482 of an endoscope 481 and a slitting for holding the tip part of an insertion part 483 of the endoscope 481. Also, the connector hanger 475 has a slitting for holding a light guide connector 484 of the endoscope 481. Also, the treatment tool hanger 476 has a slitting for holding an operating part 486 of a treatment tool 485 and a slitting for holding the tip part.

In this manner, according to the first example, an endoscope, tools and so on can be hung on the hangers 474, 475 and 476 on the side of the bed 471.

Figure 24:
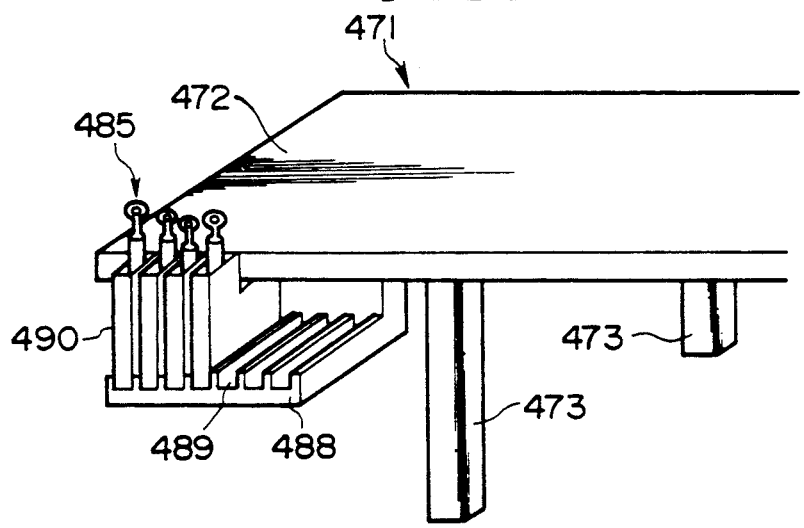
Figure 25:
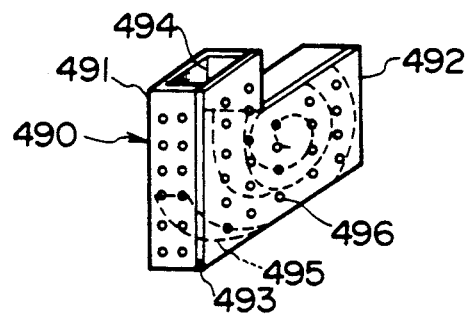

FIGS. 24 and 25 show a second example. In this example, a cassette receiver 488 is attached to one side of the bed body 472. On the cassette receiver 488, a plurality of ditches 489 are formed so as to be able to removably store cassettes 490. As shown in FIG. 25, the cassette 490 is formed into a box by a body 491 and a cover 492 fitted to the body 491 with a hinge 493. On a part of the box, a tool insertion hole 494 is provided. Also, in the inner part of the cassette 490, a spiral space leading to the tool insertion hole 494 is formed with a spiral partition 495. Then, if the treatment tool 485 is inserted into the tool insertion hole 494, an insertion part of the treatment tool 485 is also spiraled along said partition 495 and can be stored in a small space.

By opening said cover 492, the inner part of the cassette 490 can be washed.

Also, many vents 496 are formed on the sides of the cassette 490 so that the treatment tool 485 can be disinfected by an autoclave, gas, chemicals and so on while the treatment tool 485 is stored in the cassette 490.

Thus, according to the second example, an operator can easily take the treatment tool 485 in and out of the cassette 490.

Figure 26:
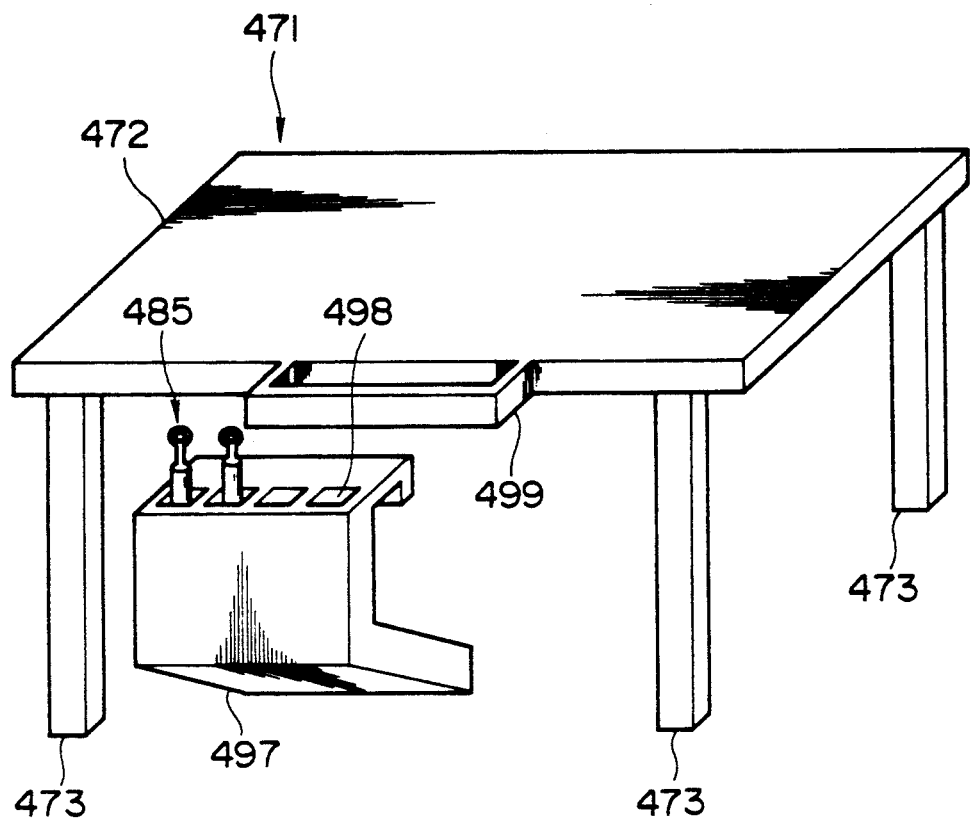

FIG. 26 shows a third example. In this example, a treatment tool container 497 having a plurality of treatment tool insertion holes 498 is provided and a hanger 499 by which said treatment tool container 497 is hung is provided on one side of the bed body 472.

In this example, according to a treatment, the treatment tool container 497 in which the treatment tool 485 suitable for the treatment was stored in advance of the treatment can be exchanged so that the time for preparation can be shortened.

In the meantime, in the case in which an endoscope image obtained by a television camera attached to an eyepiece part of an electronic scope and fiberscope is displayed on a monitor and examined, the monitor has been placed on the side of the bed. However, even if the monitor was placed on the side of the bed, the monitor and the subject could not be looked with a single glance because the monitor was arranged at some distance from the subject. Also, an endoscope examination monitor has been put on a table on which a light source device, a video processor and so on are placed. Thus, if the monitor is moved, other light source device and others are also moved so that the endoscope operation tends to be difficult for the operator according to circumstances.

Then, FIGS. 27 to 31 show examples in which a monitor and a subject can be looked with a single glance by providing a monitor or an adapter for attaching a monitor.

Figure 27:
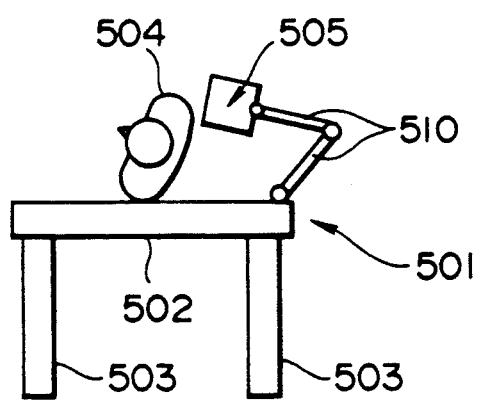
FIGS. 27 to 31 relate to the example in which a monitor or an adapter for attaching the monitor is provided in a bed.

FIG. 27 is an illustration showing a bed of a first example. In this example, a bendable arm 510 is fitted to a bed body 502 and a monitor 505 is fitted to the tip part of the arm 510. During the examination, the monitor 505 is placed near the head of a subject 504.

According to this example, since there is no obstacle between the operator and the subject, the examination is easily performed.

Figure 28:
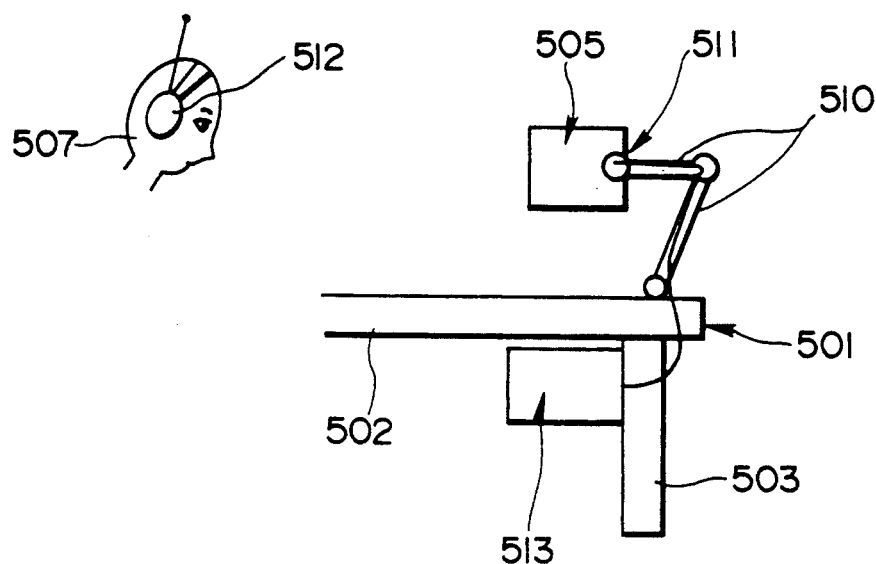

FIG. 28 shows a second example. In this example, the monitor 505 is fitted to the bed body 502 through the bendable arm 510. A position control motor 511 for changing the direction of the monitor 505 is provided on the tip part of the arm 510.

Also, an operator 507 is fitted with a transmitter 512 on the head and a control device 513 including a receiver and a CPU is provided under the bed body 502. The control device 513 receives a signal from said transmitter 512 by the receiver so that the position of the operator is judged by the CPU and the position control motor 511 is controlled so as to turn the monitor 505 to the direction of the operator.

According to this example, the monitor 505 always faces the same side as of the operator 507.

Also, in each example mentioned above, the monitor may be a liquid crystal monitor. Since the liquid crystal monitor is thin, the monitor can be easily installed on the bed and the monitor does not become an obstacle during the examination.

Figure 29:
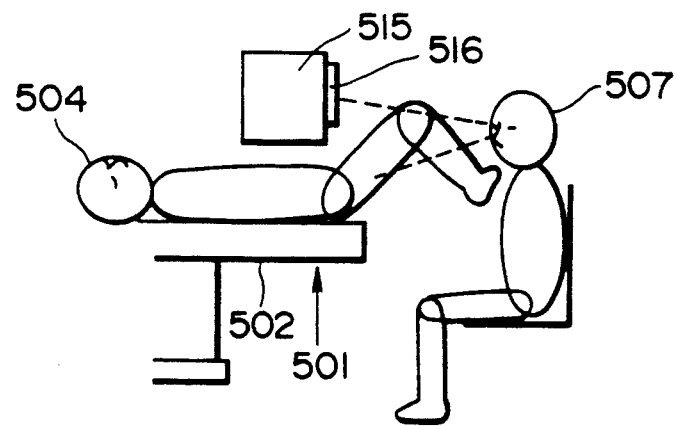

FIG. 29 shows a third example. In this example, an X-ray camera or the like is fitted to a C arm 515 provided above the bed body 502, and a liquid crystal television 516 for displaying an endoscope image is attached to the C arm 515 so that both the operator 507 and the subject 504 can watch the liquid crystal television 516.

Also, in each example mentioned above, if a plurality of monitors needed for the examination, which include not only a monitor for endoscope image but also a monitor for X-ray image and others, are attached to the bed, all monitors can be viewed with a look.

Figure 30:
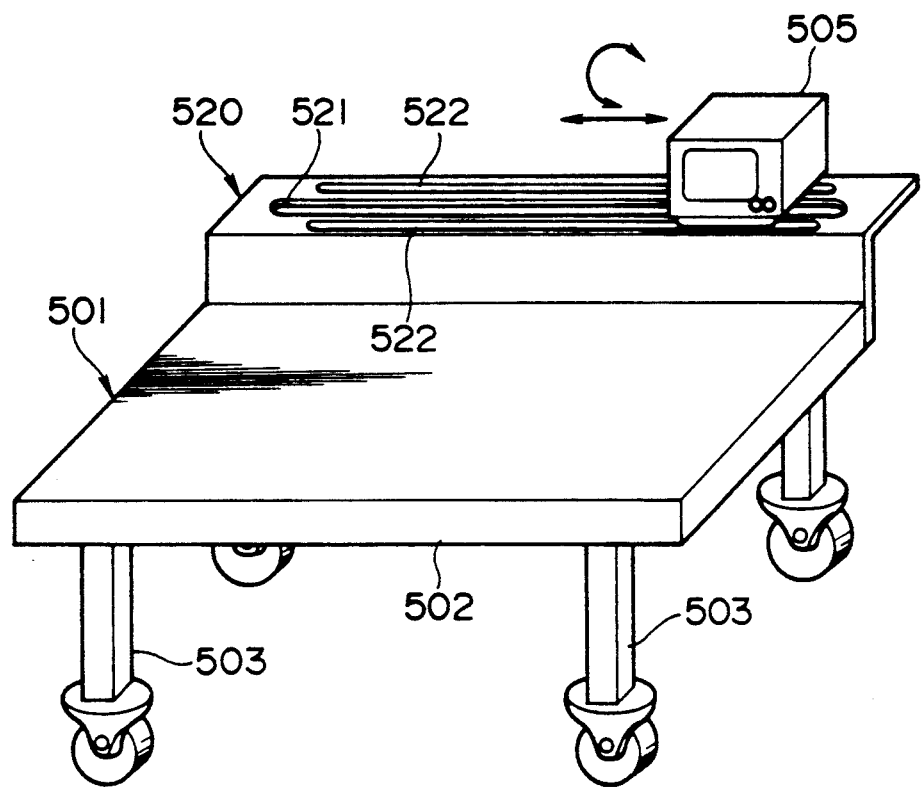
Figure 31:
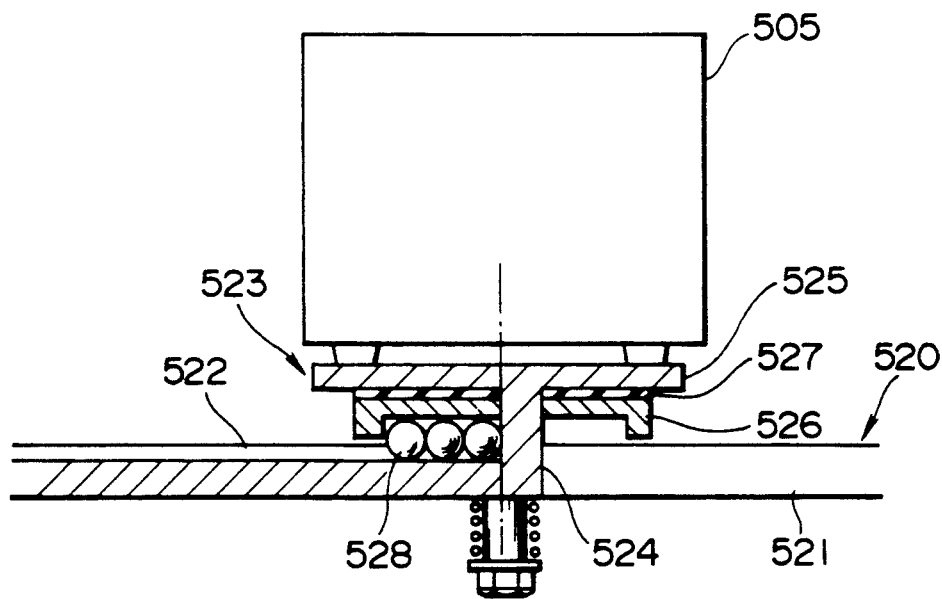

FIGS. 30 and 31 relate to a fourth example. In this example, a rail part 520 is provided on a side of a bed body 502. On the rail part 520, a long hole 521 is formed in the center part along the lengthwise direction of the bed and ditches 522 and 522 are formed on both sides of the long hole 521. On the rail part 520, a monitor stand 523 is provided. The monitor stand 523 has a shaft part 524 inserted into said long hole 521 and a plate-shaped monitor receiving part 525. The monitor 505 is placed on the surface of the monitor receiving part 525. Also, a ball receiver 526 is provided between the bottom of said monitor receiving part 525 and the surface of the rail part 520. On the surface of the ball receiver 526, a Teflon sheet 527 is attached so that the surface of the ball receiver 526 and the bottom of the monitor receiving part 525 are slidable. Also, a plurality of balls 528 are applied between said bottom of ball receiver 526 and said ditches 522.

By this structure, the monitor stand 523 is movable in the lengthwise direction of the rail part 520. Also, the monitor stand 523 is rotatable around the shaft part 524.

According to this example, the monitor 505 can be arranged on the position on which the operator can easily watch the monitor. Also, the rail part 520 may be provided around the whole peripheral part of the bed body 502.

Also, not only the monitor 505 but also an operating panel, a light source device, a video processor and so on may be movably provided on the sides of the bed.

An endoscope examination may be performed under a fluoroscopy. At that time, although it is necessary that the tip of the insertion part of an endoscope is set within the scope of fluoroscopy, in the case in which the tip is moved a vast range, especially in the large intestine examination or the like, the tip tends to be off the scope of fluoroscopy. In this case, up to the present, the operator or engineer moved the bed; however, it was dreadful work.

Figure 32:
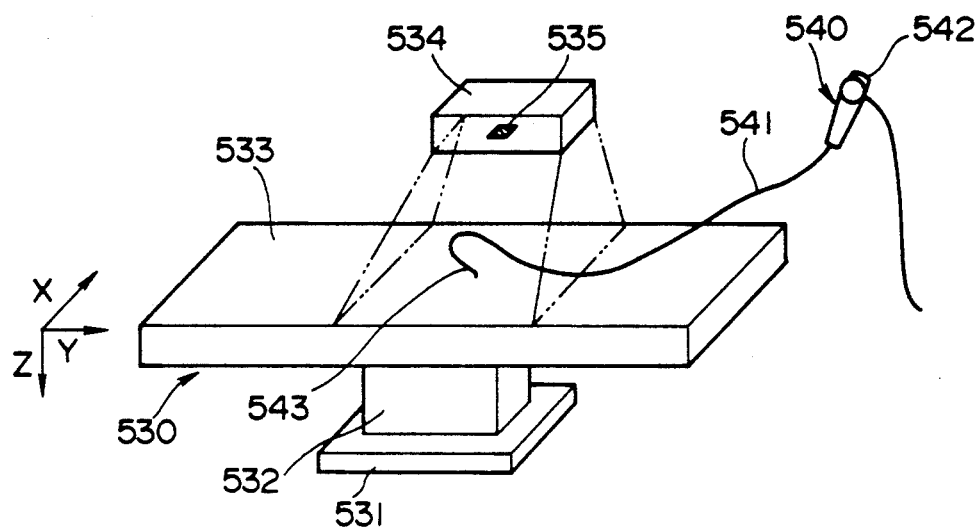
FIGS. 32 to 34 relate to the example in which a bed is moved according to processed signals from a transmitter provided at the tip of an endoscope.
Figure 33:
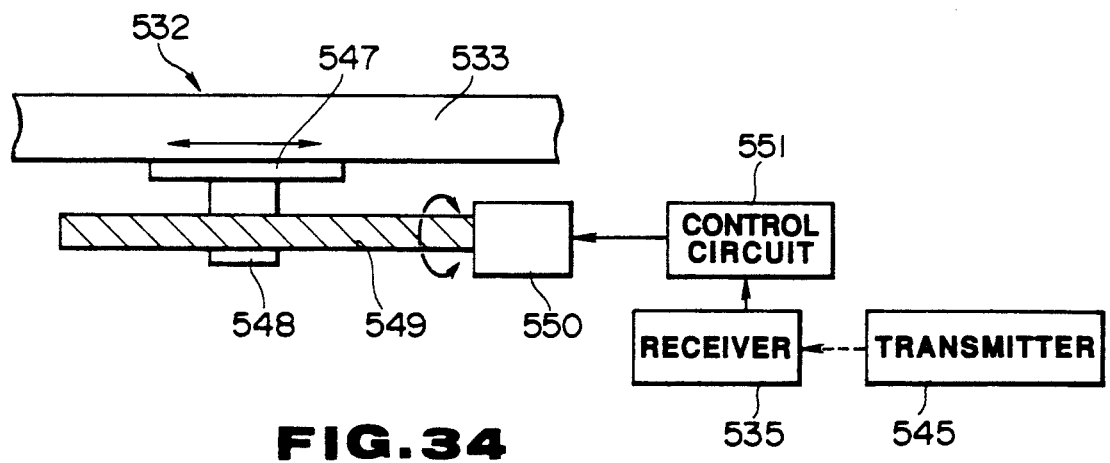
Figure 34:
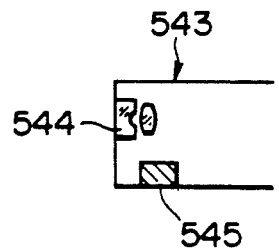

Then, FIGS. 32 to 34 show an example which is designed to reduce the labor of the examination by processing signals from the transmitter provided on the tip of the endoscope so as to move the bed.

A bed 530 in this example comprises a stand 531, a driving part 532 provided on the stand 531 and a bed body 533 provided on the driving part 532. A C arm 534 for attaching an X-ray camera or the like is provided above the bed body 533 and a receiver 535 is provided near the center part of the C arm 534.

On the other hand, an endoscope 540 comprises an elongated insertion part 541 and an operating part 542 provided on the end of the insertion part 541. Near an objective lens 544, a transmitter 545 is provided on the tip part 543 of the insertion part 541 as shown in FIG. 34.

The driving part 532 is formed as shown in FIG. 33. That is, a moving nut 548 is fitted to the bed body 533 through a moving stand 547 and a bolt 549 is spirally fitted to the moving nut 548. The bolt 549 is driven and rotated by a motor 550. By rotating this motor 550, the bolt 549 is rotated and then, the moving nut 548, the moving stand 547 and the bed body 533 are moved in the direction of the arrow in FIG. 33. The rotation of the motor 550 is controlled by a control circuit 551 in response to the signal from the receiver 535. Also, two sets of motors 550, bolts 549, moving nuts 548 and moving stands 547, are provided so that their respective moving directions meet at right angles. Therefore, the bed body 533 can be moved in two directions (X and Y directions in FIG. 32) meeting at a right angle.

In this example, the signal from the transmitter 545 provided on the tip part 543 of the endoscope 540 is received by the receiver 535 provided in the C arm 534 and the position of the tip part 543 is detected by the receiver 535. According to the position of the tip part 543, the motor 550 is driven by the control circuit 551 and the bed body 533 is moved so that the tip part 543 can enter the scope of fluoroscopy.

Figure 35:
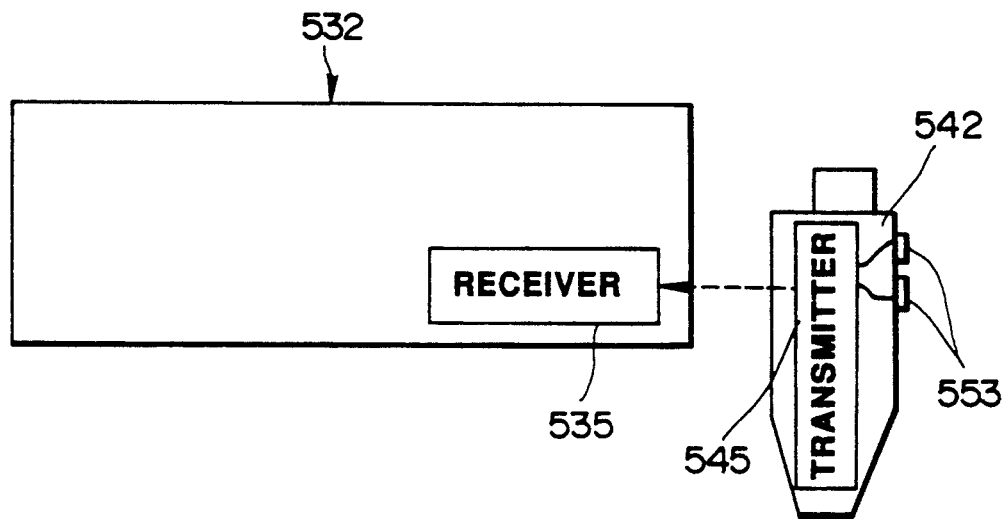
FIG. 35 is an illustration of the example in which a switch for operating a bed is provided in an operating part of an endoscope.

Also, as shown in FIG. 35, the bed body 533 may be moved by operating bed operation switches 553 and 553 provided in the operating part 542 of the endoscope. In this example, switches 553 and 553 are connected to the transmitter 545 provided in the operating part 542. The signals from switches 553 and 553 are transmitted by the transmitter 545 and received by the receiver 535 provided in the driving part 532 shown in FIG. 33. Then, the bed body 533 is moved by the control circuit 551 based on the signal from the receiver 535.

Also, the control circuit 551 and the switches 553 and 553 may be connected by a connection without passing through the transmitter and receiver.

Figure 36:
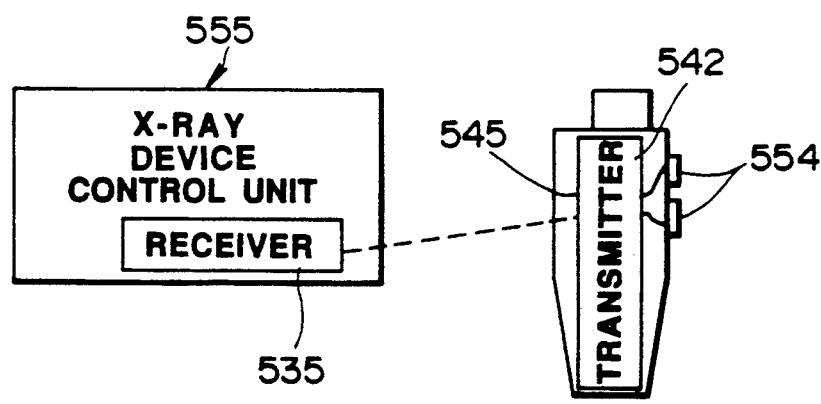
FIG. 36 is an illustration of the example in which a switch for operating an X-ray device is provided in an operating part of an endoscope.

Further, as shown in FIG. 36, an X-ray photography may be controlled by operating X-ray photography operating switches 554 and 554 provided in the operating part 542 of the endoscope. In this example, switches 554 and 554 are connected to a transmitter 545 provided in operating part 542. The signals from said switches 554 and 554 are transmitted by the transmitter 545 and received by the receiver 535 provided in an X-ray device control unit for controlling an X-ray device. Then, the X-ray device is controlled based on the signal from the receiver 535.

Also, the X-ray device control unit and the switches 554 and 554 may be connected by a connection without passing through the transmitter and receiver.

In this invention, it is apparent that working modes different in a wide range can be formed on this invention without departing from the spirit and scope of the invention. This invention is not restricted by its specific working modes except being limited by the appended claims.

What is claimed is:

1. An endoscope examination apparatus comprising:
    a bed on which a subject lies;
    an examination device positioned separately from said bed and used for an endoscope examination;
    a single control means provided in said bed for controlling said examination device;
    a connecting means for operatively connecting said examination device and said control means, said connecting means including a part extended from said bed and connected to said examination device,
    a plurality of connectors spaced about a peripheral part of said bed providing communication with said control means; and
    at least one operating means detachably connected to at least one of said connectors for permitting the operator to manipulate said examination device through said control means.

2. An apparatus according to claim 1, wherein said examination device is an endoscope light source device, wherein said connecting means provides for connection of an endoscope and said light source device.

3. The apparatus of claim 1, including a plurality of operating means wherein
    each said operating means has the same function.

4. The apparatus of claim 1, wherein said operating means comprises a display part and an input part.

5. An endoscope examination apparatus comprising:
    an examination bed on which a subject lies;
    a device used for an endoscope examination;
    at least one operating means provided on a peripheral part of said bed for allowing the operator to operate said device; and
    a connecting means for removably connecting said device and said operating means, said connecting means including a plurality of connectors spaced about the sides of said bed,
    wherein said operating means may be removably connected with any one of said connectors to permit operation of said device.

6. An apparatus according to claim 5, wherein said device comprises at least an endoscope signal processing device, wherein said endoscope signal processing device is controlled by a control means and said operating means to process image information from said device used for an endoscope examination which is operatively attached to said signal processing device.

7. An apparatus according to claim 5, wherein said device is an endoscope light source device, wherein said connecting means includes provided in said bed for connecting an endoscope and said light source device.

8. The apparatus of claim 5, further comprising:
a plurality of said operating means each having the same function which can be connected to said plurality of connectors.

9. The apparatus of claim 5, wherein said operating means comprises a display part and an input part.

10. The apparatus of claim 5, further comprising:
a single control device provided in said bed for controlling said examination device, wherein said connecting means removably connects said operating means to said control device and said connecting means removably connects said examination device to said control device;
an address bus connected between said control device and said examination device; and
a data bus connected between said control device and said examination device.

11. An endoscope examination apparatus comprising:
a bed on which a subject lies;
a single control device provided in said bed for controlling an endoscope examination device separately positioned from said bed;
a first connecting means for operatively connecting said endoscope examination device and said control device, said first connecting means including a part extended from said bed and connected to said endoscope examination device;
a plurality of connectors spaced about a peripheral part of said bed and connected to said control device; and
at least one operating means detachably connected to any one of said connectors, wherein said operating means is connected through at least one of said connectors to said control device for permitting the operator to manipulate said endoscope examination device.

12. The apparatus of claim 11 further comprising:
a plurality of said operating means, provided on a peripheral part of said bed for operating said examination device, each having the same function, connected to said control device through said plurality of connectors.

13. The apparatus of claim 11, wherein said operating means comprises a display part and an input part.

* * * * *